United States Patent
Bates et al.

(10) Patent No.: US 11,679,098 B2
(45) Date of Patent: *Jun. 20, 2023

(54) METHODS FOR TREATING DISEASES

(71) Applicant: UNIVERSITY OF LOUISVILLE RESEARCH FOUNDATION, INC., Louisville, KY (US)

(72) Inventors: Paula J. Bates, Louisville, KY (US); Sarah A. Andres, Floyds Knobs, IN (US); Joseph A. Burlison, Louisville, KY (US); Levi Beverly, Louisville, KY (US); Nagaraju Miriyala, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,027

(22) Filed: Oct. 9, 2019

(65) Prior Publication Data

US 2020/0108050 A1    Apr. 9, 2020

Related U.S. Application Data

(60) Provisional application No. 62/743,397, filed on Oct. 9, 2018.

(51) Int. Cl.
| | | |
|---|---|---|
| *A61K 31/045* | (2006.01) | |
| *A61K 31/4188* | (2006.01) | |
| *A61K 31/08* | (2006.01) | |
| *A61K 31/035* | (2006.01) | |
| *A61K 31/351* | (2006.01) | |
| *A61K 31/133* | (2006.01) | |
| *A61K 31/085* | (2006.01) | |
| *A61K 31/095* | (2006.01) | |
| *A61K 31/22* | (2006.01) | |
| *A61K 31/121* | (2006.01) | |

(52) U.S. Cl.
CPC ........ *A61K 31/4188* (2013.01); *A61K 31/035* (2013.01); *A61K 31/045* (2013.01); *A61K 31/08* (2013.01); *A61K 31/085* (2013.01); *A61K 31/095* (2013.01); *A61K 31/121* (2013.01); *A61K 31/133* (2013.01); *A61K 31/22* (2013.01); *A61K 31/351* (2013.01)

(58) Field of Classification Search
CPC .............................. A61K 31/035; C07C 33/483
See application file for complete search history.

(56) References Cited

U.S. PATENT DOCUMENTS

| | | | | |
|---|---|---|---|---|
| 8,207,381 B2* | 6/2012 | Hammond | ............ | C07C 69/007 568/843 |
| 8,703,829 B2* | 4/2014 | Hammond | .............. | C07C 33/42 514/745 |
| 9,383,364 B2* | 7/2016 | Bates | .................. | A61K 31/045 |
| 9,737,493 B2* | 8/2017 | Salipur | .................. | A61K 45/06 |
| 2008/0188570 A1 | 8/2008 | Hammond et al. | | |
| 2014/0329911 A1* | 11/2014 | Bates | ..................... | C07K 16/18 514/739 |
| 2016/0177399 A1* | 6/2016 | Meng | .................. | C12Q 1/6886 506/2 |

FOREIGN PATENT DOCUMENTS

WO    WO-2008098077 A2 *  8/2008    .............. A61P 43/00

OTHER PUBLICATIONS

Chaib et al. Neoplasia, 2001, vol. 3, No. 1, pp. 43-52 (Year: 2001).*
Linnerth et al. Int. J. Cancer, 2005, vol. 114, pp. 977-982 (Year: 2005).*
Johansson et al. Carcinogenesis, 2007, vol. 28, No. 2, pp. 465-470 (Year: 2007).*
Scotlandi et al. Journal of Clinical Oncology, 2009, vol. 27, No. 13, pp. 2209-2216 (Year: 2009).*
Hetland et al. Gynecologic Oncology, 2012, vol. 126, pp. 460-465 (Year: 2012).*
Kelner et al. Free Radical Biology and Medicine, 2014, vol. 69, pp. 167-171 (Year: 2014).*
Bates et al. "Antiproliferative activity of G-rich oligonucleotides correlates with protein binding" J Biol Chem. (1999) vol. 274, No. 37, pp. 26369-26377.
Comess et al. (2018) "Emerging Approaches for the Identification of Protein Targets of Small Molecules—A Practitioners' Perspective" J. Med. Chem., vol. 61, No. 19, pp. 8504-8535.
Deponte (2013) "Glutathione catalysis and the reaction mechanisms of glutathione-dependent enzymes" Biochimica et Biophysica Acta, vol. 1830, No. 5, pp. 3217-3266.
Gmeiner et al. (2010) "Genome-Wide mRNA and microRNA Profiling of the NCI 60 Cell Line Screen and Comparison of FdUMP[10] with fluorouracil, floxuridine, and Top1 Poisons" Mol Cancer Ther., vol. 9, No. 12, pp. 3105-3114.
Hoye et al. (2007) "Mosher ester analysis for the determination of absolute configuration of stereogenic (chiral) carbinol carbons" Nat Protoc., vol. 2, No. 10, pp. 2451-2458.
Johansson et al. (2007) "Microsomal glutathione transferase 1 in anticancer drug resistance" Carcinogenesis, vol. 28, pp. 465-470.
Liu et al. (2012)"Efficient synthesis of unsymmetrical S-(bromodifluoromethyl)diarylsulfonium salts for electrophilic bromodifluoromethylating reagents" New J. Chem., vol. 36, pp. 1769-1773.
Morgan (1998) "Tetrazolium (MTT) assay for cellular viability and activity" Methods Mol Biol., vol. 79, pp. 179-183.

(Continued)

*Primary Examiner* — James D. Anderson
(74) *Attorney, Agent, or Firm* — Algm LLP; Harry J. Guttman

(57) ABSTRACT

Some embodiments of the invention include methods of using a compound such as Formula (I), Formula (II), or I-1 (e.g., in compositions or in pharmaceutical compositions) for treating diseases (e.g., cancer such as chemo-resistant cancer or cancer-therapy-resistant cancer). Additional embodiments of the invention are also discussed herein.

21 Claims, 6 Drawing Sheets

Specification includes a Sequence Listing.

(56) References Cited

OTHER PUBLICATIONS

Morgenstern et al. (2011) "Microsomal glutathione transferase 1: mechanism and functional roles" Drug Metab Rev, vol. 43, pp. 300-306.
Salipur et al. (2014) "A novel small molecule that induces oxidative stress and selectively kills malignant cells" Free Radic Biol Med, vol. 68, pp. 110-121.
Shoemaker (2006) "The NCI60 human tumour cell line anticancer drug screen" Nat Rev Cancer, vol. 6, No. 10, pp. 813-823.
UniProtKB—P10620 (MGST1_Human) (1989).
UniProtKB—Q91VS7 (MGST1_Mouse) (2004).
Van Gisbergen et al. (2016) "Chemical Reactivity Window Determines Prodrug Efficiency toward Glutathione Transferase Overexpressing Cancer Cells" Mol Pharm., vol. 13, No. 6, pp. 2010-2025.
Xu et al. (2006) "An efficient synthesis of difluoropropargyl bromides" Synthesis, vol. 5, pp. 803-806.
Yamazaki et al. (1995) "Modified Preparation Method of Trifluoromethylated Propargylic Alcohols and Its Application to Chiral 2, 6-Dideoxy-6, 6, 6-trifluoro sugars" J. Org. Chern., vol. 60, No. 19, pp. 6046-6056.
Yoshida et al. (2004) "Palladium-catalysed cascade ring expansion reaction of cyclobutanols that have a propargylic moiety with nucleophiles" Org Biomol Chem., vol. 2, No. 21, pp. 3099-3107.
Paull et al. (1989) "Display and Analysis of Patterns of Differential Activity of Drugs Against Human Tumor Cell Lines: Development of Mean Graph and Compare Algorithm" J Natl Cancer Inst, vol. 81, pp. 1088-1092.

\* cited by examiner

SEQUENCE LISTING

<160> NUMBER OF SEQ ID NOS: 11

<210> SEQ ID NO 1
<211> LENGTH: 75
<212> TYPE: DNA
<213> ORGANISM: Artificial Sequence
<220> FEATURE:
<223> OTHER INFORMATION: Forward primer 1
<220> FEATURE:
<221> NAME/KEY: misc_feature
<222> LOCATION: (34)..(48)
<223> OTHER INFORMATION: n is a, c, g, or t

<400> SEQUENCE: 1
tcgtcggcag cgtcagatgt gtataagaga cagnnnnnnn nnnnnnnntc ttgtggaaag    60
gacgaaacac cgvac                                                     75

<210> SEQ ID NO 2
<211> LENGTH: 74
<212> TYPE: DNA
<213> ORGANISM: Artificial Sequence
<220> FEATURE:
<223> OTHER INFORMATION: Forward primer 2
<220> FEATURE:
<221> NAME/KEY: misc_feature
<222> LOCATION: (34)..(47)
<223> OTHER INFORMATION: n is a, c, g, or t

<400> SEQUENCE: 2
tcgtcggcag cgtcagatgt gtataagaga cagnnnnnnn nnnnnnntct tgtggaaagg    60

```
acgaaacacc gvac                                              74

<210> SEQ ID NO 3
<211> LENGTH: 73
<212> TYPE: DNA
<213> ORGANISM: Artificial Sequence
<220> FEATURE:
<223> OTHER INFORMATION: Forward primer 3
<220> FEATURE:
<221> NAME/KEY: misc_feature
<222> LOCATION: (34)..(46)
<223> OTHER INFORMATION: n is a, c, g, or t

<400> SEQUENCE: 3
tcgtcggcag cgtcagatgt gtataagaga cagnnnnnnn nnnnnntctt gtggaaagga   60
cgaaacaccg vac                                               73

<210> SEQ ID NO 4
<211> LENGTH: 72
<212> TYPE: DNA
<213> ORGANISM: Artificial Sequence
<220> FEATURE:
<223> OTHER INFORMATION: Forward primer 4
<220> FEATURE:
<221> NAME/KEY: misc_feature
<222> LOCATION: (34)..(45)
<223> OTHER INFORMATION: n is a, c, g, or t

<400> SEQUENCE: 4
tcgtcggcag cgtcagatgt gtataagaga cagnnnnnnn nnnntcttg tggaaaggac    60 gaaacaccgv ac                                                72

<210> SEQ ID NO 5
<211> LENGTH: 71
<212> TYPE: DNA
<213> ORGANISM: Artificial Sequence
<220> FEATURE:
<223> OTHER INFORMATION: Forward primer 5
<220> FEATURE:
<221> NAME/KEY: misc_feature
<222> LOCATION: (34)..(44)
<223> OTHER INFORMATION: n is a, c, g, or t

<400> SEQUENCE: 5
tcgtcggcag cgtcagatgt gtataagaga cagnnnnnnn nnnntcttgt ggaaaggacg   60
aaacaccgva c                                                 71

<210> SEQ ID NO 6
<211> LENGTH: 70
<212> TYPE: DNA
<213> ORGANISM: Artificial Sequence
<220> FEATURE:
<223> OTHER INFORMATION: Forward primer 6
<220> FEATURE:
<221> NAME/KEY: misc_feature
<222> LOCATION: (34)..(43)
<223> OTHER INFORMATION: n is a, c, g, or t

<400> SEQUENCE: 6
tcgtcggcag cgtcagatgt gtataagaga cagnnnnnnn nnntcttgtg gaaaggacga   60 aacaccgvac                                                   70

<210> SEQ ID NO 7
<211> LENGTH: 69
<212> TYPE: DNA
<213> ORGANISM: Artificial Sequence
```

```
<220> FEATURE:
<223> OTHER INFORMATION: Forward primer 7
<220> FEATURE:
<221> NAME/KEY: misc_feature
<222> LOCATION: (34)..(42)
<223> OTHER INFORMATION: n is a, c, g, or t

<400> SEQUENCE: 7
tcgtcggcag cgtcagatgt gtataagaga cagnnnnnnn nntcttgtgg aaaggacgaa      60 acaccgvac                                                             69

<210> SEQ ID NO 8
<211> LENGTH: 68
<212> TYPE: DNA
<213> ORGANISM: Artificial Sequence
<220> FEATURE:
<223> OTHER INFORMATION: Forward primer 8
<220> FEATURE:
<221> NAME/KEY: misc_feature
<222> LOCATION: (34)..(41)
<223> OTHER INFORMATION: n is a, c, g, or t

<400> SEQUENCE: 8
tcgtcggcag cgtcagatgt gtataagaga cagnnnnnnn ntcttgtgga aaggacgaaa      60 caccgvac                                                              68

<210> SEQ ID NO 9
<211> LENGTH: 67
<212> TYPE: DNA
<213> ORGANISM: Artificial Sequence
<220> FEATURE:
<223> OTHER INFORMATION: Forward primer 9
<220> FEATURE:
<221> NAME/KEY: misc_feature
<222> LOCATION: (34)..(40)
<223> OTHER INFORMATION: n is a, c, g, or t

<400> SEQUENCE: 9
tcgtcggcag cgtcagatgt gtataagaga cagnnnnnnn tcttgtggaa aggacgaaac      60 accgvac                                                               67

<210> SEQ ID NO 10
<211> LENGTH: 66
<212> TYPE: DNA
<213> ORGANISM: Artificial Sequence
<220> FEATURE:
<223> OTHER INFORMATION: Forward primer 10
<220> FEATURE:
<221> NAME/KEY: misc_feature
<222> LOCATION: (34)..(39)
<223> OTHER INFORMATION: n is a, c, g, or t

<400> SEQUENCE: 10
tcgtcggcag cgtcagatgt gtataagaga cagnnnnnnt cttgtggaaa ggacgaaaca      60 ccgvac                                                                66

<210> SEQ ID NO 11
<211> LENGTH: 64
<212> TYPE: DNA
<213> ORGANISM: Artificial Sequence
<220> FEATURE:
<223> OTHER INFORMATION: Reverse primer
```

```
<400> SEQUENCE: 11
gtctcgtggg ctcggagatg tgtataagag acagtatgtc tactattctt tcccctgcac    60
tgta                                                                  64
```

METHODS FOR TREATING DISEASES

CROSS-REFERENCE TO RELATED APPLICATIONS

This application claims the benefit of U.S. Provisional Application No. 62/743,397, filed Oct. 9, 2018 entitled "METHODS TO TREAT CANCER" which is herein incorporated by reference in its entirety.

GOVERNMENT RIGHTS

This invention was made with government support under GM106396 awarded by National Institutes of Health. The government has certain rights in the invention.

REFERENCE TO A SEQUENCE LISTING

The instant application contains a Sequence Listing that has been submitted in ASCII format via EFS-Web and is hereby incorporated by reference in its entirety. Said ASCII copy, created on Oct. 1, 2019, is named 2019_10_seq_listing_35783_04134_ST25.txt and is 3.91 KB in size.

BACKGROUND

Several compounds are known to treat diseases, such as cancer, but do so inadequately. For example, some platinum-containing drugs can be effective anticancer therapies, but they can sometimes have side effects, such as toxicity. Attempts to design compounds have not always yielded effective anticancer agents and are not always as less toxic to non-cancer cells as would be desired.

Certain embodiments of the invention address one or more of the deficiencies described above. Some embodiments of the invention include methods of using a compound such as Formula (I), Formula (II), or I-1 (e.g., in compositions or in pharmaceutical compositions) for treating diseases (e.g., cancer such as chemo-resistant cancer or cancer-therapy-resistant cancer). Additional embodiments of the invention are also discussed herein.

SUMMARY

Some embodiments of the present invention include a method for treating an animal for cancer. In other embodiments, the method comprises determining a level of MGST1 (microsomal glutathione S-transferase) in a sample comprising cancer cells from an animal having a cancer; and administering one or more compositions comprising a compound. In yet other embodiments, the compositions may be the same or different if there is more than one administration. In still other embodiments, the compound is selected from Formula (I) and salts, optical isomers, geometric isomers, salts of isomers, and derivatives thereof:

(I).

In certain embodiments, $R_1$ is carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl, is substituted with one or more groups independently selected from halo, hydroxy, mercapto, $(C_1\text{-}C_{20})$alkoxy, $(C_2\text{-}C_{20})$alkenyloxy, $(C_2\text{-}C_{20})$alkynyloxy, aryloxy, heteroaryloxy, $(C_3\text{-}C_{20})$cycloalkyloxy, heterocyclyloxy, $(C_1\text{-}C_{20})$alkylthio, $(C_2\text{-}C_{20})$alkenylthio, $(C_2\text{-}C_{20})$alkynylthio, carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, cycloalkyl, heterocyclyl, $NR_aR_b$, $(C_2\text{-}C_{20})$alkynoyloxy, and arylcarbonyloxy. In other embodiments, $R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$, or $CCl_3$. In still other embodiments, each $R_a$ and $R_b$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, $(C_2\text{-}C_{20})$alkynyloxy, or aryl-$(C_1\text{-}C_{20})$alkoxycarbonyl. In some embodiments, each $R_c$ and $R_d$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In certain embodiments, $R_e$ is $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In other embodiments, each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1\text{-}C_{20})$alkyl, $(C_2\text{-}C_{20})$alkenyl, $(C_2\text{-}C_{20})$alkynyl, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, aryl$(C_1\text{-}C_{20})$alkyl, heteroaryl$(C_1\text{-}C_{20})$alkyl, aryl$(C_2\text{-}C_{20})$alkenyl, aryl$(C_2\text{-}C_{20})$alkynyl, heteroaryl$(C_2\text{-}C_{20})$alkenyl, heteroaryl$(C_2\text{-}C_{20})$alkynyl, $(C_1\text{-}C_{20})$alkanoyloxy, $(C_2\text{-}C_{20})$alkenoyloxy, and $(C_2\text{-}C_{20})$alkynoyloxy.

In some embodiments, $R_1$ is carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl, is substituted with one or more groups independently selected from halo, hydroxy, mercapto, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, and $NR_aR_b$. In other embodiments, $R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, or $CCl_3$. In yet other embodiments, each $R_a$ and $R_b$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In still other embodiments, each $R_c$ and $R_d$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In certain embodiments, $R_e$ is $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In some embodiments, each aryl or heteroaryl of $R_1$ is optionally substituted with one or more groups independently selected from halo, hydroxy, nitro, cyano, trifluoromethyl, trifluoromethoxy, mercapto, carboxy, $(C_1\text{-}C_{20})$alkyl, $(C_2\text{-}C_{20})$alkenyl, $(C_2\text{-}C_{20})$alkynyl, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, aryl$(C_1\text{-}C_{20})$alkyl, heteroaryl$(C_1\text{-}C_{20})$alkyl, aryl$(C_2\text{-}C_{20})$alkenyl, aryl$(C_2\text{-}C_{20})$alkynyl, heteroaryl$(C_2\text{-}C_{20})$alkenyl, heteroaryl$(C_2\text{-}C_{20})$alkynyl, $(C_1\text{-}C_{20})$alkanoyloxy, $(C_2\text{-}C_{20})$alkenoyloxy, and $(C_2\text{-}C_{20})$alkynoyloxy.

In some embodiments, the compound is not 6-bromo-6,6-difluoro-2-methylhex-4-yn-3-ol. In some embodiments, $R_1$ is a $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl is substituted with hydroxy, mercapto, carboxy or $NR_aR_b$. In other embodiments, $R_1$ is a $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl is substituted with hydroxy. In certain embodiments, wherein $R_1$ is a $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl is substituted on the carbon adjacent to the triple bond in Formula (I) with hydroxy. In still other embodiments, $R_1$ is a $(C_5$-$C_{10})$alkyl, $(C_2$-$C_{10})$alkenyl, or $(C_2$-$C_{10})$alkynyl that is substituted with hydroxy, mercapto, carboxy, or $NR_aR_b$. In yet other embodiments, $R_1$ is a $(C_5$-$C_{10})$alkyl, $(C_2$-$C_{10})$alkenyl, or $(C_2$-$C_{10})$alkynyl that is substituted with hydroxyl. In certain embodiments, $R_1$ is a $(C_5$-$C_{10})$alkyl, $(C_2$-$C_{10})$alkenyl, or $(C_2$-$C_{10})$alkynyl that is substituted on the carbon adjacent to the triple bond in Formula (I) with hydroxy. In some embodiments, $R_1$ is a $(C_5$-$C_{10})$alkyl that is substituted with hydroxy, mercapto, carboxy or $NR_aR_b$. In other embodiments, $R_1$ is a $(C_5$-$C_{10})$alkyl that is substituted with hydroxy. In still other embodiments, $R_1$ is a $(C_5$-$C_{10})$alkyl that is substituted on the carbon adjacent to the triple bond in Formula (I) with hydroxy. In yet other embodiments, $R_1$ is $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl is substituted with $(C_1$-$C_{20})$alkanoyloxy. In certain embodiments, $R_1$ is a $(C_5$-$C_{10})$alkyl that is substituted on the carbon adjacent to the triple bond in Formula (I) with $(C_1$-$C_{20})$alkanoyloxy. In some embodiments, $R_1$ is 1-hydroxyhexane, 1-hydroxy-2,2-dimethylpropane, 1-acetoxyhexane or cis-1-hydroxy-3-hexane. In some embodiments, $R_1$ is a $(C_5$-$C_{10})$alkyl that is substituted on the carbon adjacent to the triple bond in Formula (I) with acetoxy.

In some embodiments, $R_2$ is $CF_2Br$, $CFHBr$, $CF_2Cl$, or $CFHCl$. In other embodiments, $R_2$ is $CF_2Br$.

In some embodiments, the compound is selected from Formula (II) and salts, optical isomers, geometric isomers, salts of isomers, and derivatives thereof:

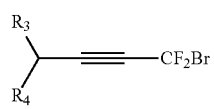

(II)

In certain embodiments, $R_3$ is hydroxy, mercapto, chloro, bromo, methylthio, ethylthio, methoxy, ethoxy, acetylamino, $(C_1$-$C_{10})$alkanoyloxy, arylcarbonyloxy, or aryloxy. In some embodiments, $R_4$ is $(C_4$-$C_{10})$alkyl, $(C_2$-$C_{10})$alkenyl, or $(C_2$-$C_{10})$alkynyl, which $(C_4$-$C_{10})$alkyl, $(C_2$-$C_{10})$alkenyl, or $(C_2$-$C_{10})$alkynyl is optionally substituted with one or more groups independently selected from halo, hydroxy, mercapto, $(C_1$-$C_{10})$alkoxy, $(C_1$-$C_{10})$alkylthio, carboxy, $(C_1$-$C_{10})$alkoxycarbonyl, aryl, heteroaryl, and $NR_aR_b$. In other embodiments, $R_3$ is hydroxy, mercapto, chloro, bromo, methylthio, ethylthio, methoxy, ethoxy, or acetylamino. In certain embodiments, $R_4$ is $(C_4$-$C_{10})$alkyl, $(C_2$-$C_{10})$alkenyl, or $(C_2$-$C_{10})$alkynyl, which $(C_4$-$C_{10})$alkyl, $(C_2$-$C_{10})$alkenyl, or $(C_2$-$C_{10})$alkynyl is optionally substituted with one or more groups independently selected from halo, hydroxy, mercapto, $(C_1$-$C_{10})$alkoxy, $(C_1$-$C_{10})$alkylthio, carboxy, $(C_1$-$C_{10})$alkoxycarbonyl, aryl, heteroaryl, and $NR_aR_b$.

In other embodiments, $R_4$ is $(C_4$-$C_{10})$alkyl that is optionally substituted with one or more groups independently selected from halo, hydroxy, mercapto, $(C_1$-$C_{10})$alkoxy, $(C_1$-$C_{10})$alkylthio, carboxy, $(C_1$-$C_{10})$alkoxycarbonyl, aryl, heteroaryl, and $NR_aR_b$. In still other embodiments, $R_4$ is $(C_4$-$C_{10})$alkyl that is optionally substituted with one or more groups independently selected from halo, hydroxy, mercapto, carboxy, $(C_1$-$C_{10})$alkoxycarbonyl, and $NR_aR_b$. In yet other embodiments, $R_4$ is $(C_4$-$C_{10})$alkyl. In certain embodiments, $R_4$ is $(C_4$-$C_6)$alkyl.

In some embodiments, the compound is 1-bromo-1,1-difluoro-4-hydroxy-5,5-dimethyl-2-hexyne, or a salt thereof. In some embodiments, the compound is XB05 or XB05a, or a salt thereof. In other embodiments, the compound is

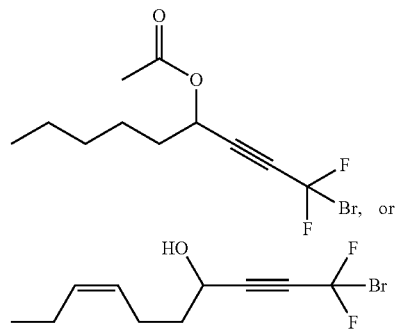

or a salt thereof.

In some embodiments, at least one of the one or more compositions further comprises a formulary ingredient. In other embodiments, at least one of the one or more compositions comprises is a pharmaceutical composition.

In some embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In certain embodiments, if there is more than one administration at least one composition used for at least one administration is different from the composition of at least one other administration.

In some embodiments, the compound of at least one of the one or more compositions is administered to the animal in an amount of from about 0.005 mg/kg animal body weight to about 50 mg/kg animal body weight.

In other embodiments, the animal is a human, a rodent, or a primate. In certain embodiments, the animal is in need of the treatment.

In some embodiments, the method is for treating acute lymphoblastic leukemia, astrocytoma, basal cell carcinoma, bladder cancer, bone marrow cancer, brain cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof. In other embodiments, the method is for treating leukemia, lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, brain cancer, breast cancer, or cancerous tumors thereof. In certain embodiments, the cancer is a chemo-resistant cancer or cancer-therapy-resistant cancer. In other embodiments, the method is for treating lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, brain cancer, breast cancer, or cancerous tumors thereof. In certain embodiments, the method is for treating cancerous tumors.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
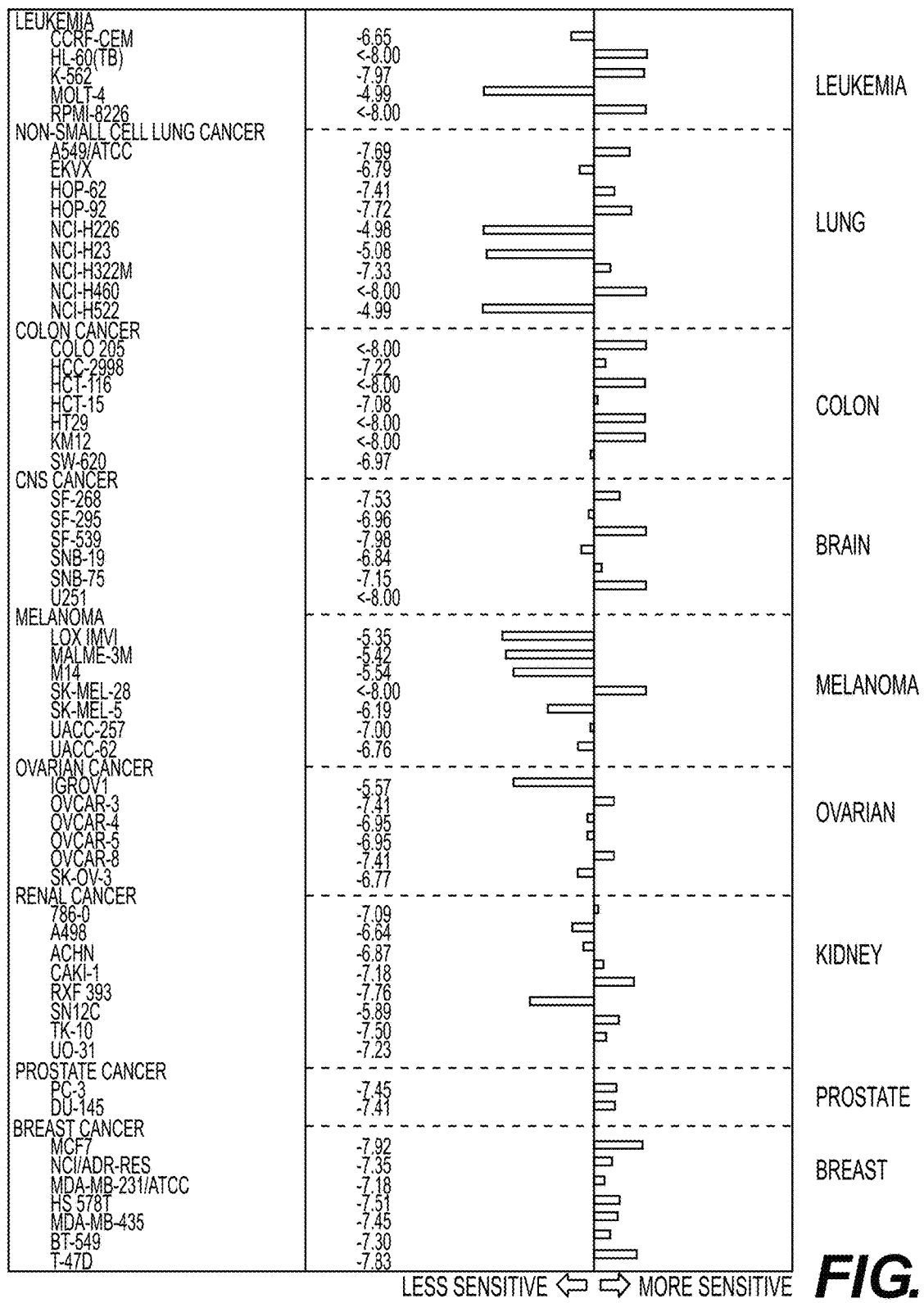
FIG. 1: Screens to Identify the role of Microsomal glutathione S-transferase 1 (MGST1). Results from the NCI's 60 human tumor cell lines screen. The COMPARE algorithm was used to probe microarray results from the cell lines to identify gene expression that correlated with this unusual pattern of growth inhibition.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include methods of using a compound such as Formula (I), Formula (II), or I-1 (e.g., in compositions or in pharmaceutical compositions) for treating diseases (e.g., cancer such as chemo-resistant cancer or cancer-therapy-resistant cancer). Additional embodiments of the invention are also discussed herein.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

The term cycloalkyl includes monocyclic or polycyclic alkyl rings containing from 3 to 12 (e.g., 3, 4, 5, 6, 7, 8, 9, 10, 11, or 12) carbon atoms.

Aryl denotes a phenyl radical or an ortho-fused bicyclic carbocyclic radical having about seven to ten (e.g., 7, 8, 9, or 10) ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent, or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocyclyl" refers to a saturated, or partially unsaturated monocyclic radical containing 4, 5, 6, or 7 atoms and at least 1 heteroatom selected from the group consisting of oxygen, sulfur, and nitrogen N(Y), wherein Y is a point of attachment, H, O, ($C_1$-$C_4$)alkyl, phenyl or benzyl, as well as a radical of a bicyclic or tricyclic ring system derived therefrom, particularly, one derived by fusing a propylene, trimethylene, or tetramethylene diradical thereto, or one derived by fusing an aryl (e.g. a benz-group) or heteroaryl ring thereto.

As used herein the term "arylcarbonyloxy" means a group of the formula aryl-C(=O)—O—, wherein aryl has the meaning described hereinabove.

As used herein the term "heteroarylcarbonyloxy" means a group of the formula heteroaryl-C(=O)—O—, wherein heteroaryl has the meaning described hereinabove.

As used herein the term "aryloxycarbonyl" means a group of the formula aryl-O—C(=O)—, wherein aryl has the meaning described hereinabove.

As used herein the term "heteroaryloxycarbonyl" means a group of the formula heteroaryl-O—C(=O)—, wherein heteroaryl has the meaning described hereinabove.

As used herein (unless otherwise specified), the term "halogen" means monovalent Cl, F, Br, or I.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be, substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Compounds and Compositions including Pharmaceutical Compositions

Examples of compounds used in the inventions are described below and some can be found in WO 2008/098077 A2 (which is herein incorporated by reference in its entirety), US 2008/0188570 A1 (which is herein incorporated by reference in its entirety), U.S. Pat. No. 9,383,364 B2 (which is herein incorporated by reference in its entirety), and U.S. Pat. No. 9,737,493 B2 (which is herein incorporated by reference in its entirety).

Compounds used in the invention can include those of Formula (I):

$$R_1\text{—}\!\equiv\!\text{—}R_2 \qquad (I).$$

and salts, optical isomers, geometric isomers, salts of isomers, and derivatives thereof. In some embodiments, $R_1$ is carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl, is substituted with one or more groups independently selected from halo, hydroxy, mercapto, $(C_1\text{-}C_{20})$alkoxy, $(C_2\text{-}C_{20})$alkenyloxy, $(C_2\text{-}C_{20})$alkynyloxy, aryloxy, heteroaryloxy, $(C_3\text{-}C_{20})$cycloalkyloxy, heterocyclyloxy, $(C_1\text{-}C_{20})$alkylthio, $(C_2\text{-}C_{20})$alkenylthio, $(C_2\text{-}C_{20})$alkynylthio, carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, cycloalkyl, heterocyclyl, $NR_aR_b$, $(C_2\text{-}C_{20})$alkynoyloxy, and arylcarbonyloxy. In other embodiments, $R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$, or $CCl_3$. In still other embodiments, each $R_a$ and $R_b$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, $(C_2\text{-}C_{20})$alkynyloxy, or aryl-$(C_1\text{-}C_{20})$alkoxycarbonyl. In yet other embodiments, each $R_c$ and $R_d$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In certain embodiments, $R_e$ is $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In some embodiments, each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1\text{-}C_{20})$alkyl, $(C_2\text{-}C_{20})$alkenyl, $(C_2\text{-}C_{20})$alkynyl, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, aryl$(C_1\text{-}C_{20})$alkyl, heteroaryl$(C_1\text{-}C_{20})$alkyl, aryl$(C_2\text{-}C_{20})$alkenyl, aryl$(C_2\text{-}C_{20})$alkynyl, heteroaryl$(C_2\text{-}C_{20})$alkenyl, heteroaryl$(C_2\text{-}C_{20})$alkynyl, $(C_1\text{-}C_{20})$alkanoyloxy, $(C_2\text{-}C_{20})$alkenoyloxy, and $(C_2\text{-}C_{20})$alkynoyloxy.

In some embodiments, $R_1$ is carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl, is substituted with one or more groups independently selected from halo, hydroxy, mercapto, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, and $NR_aR_b$. In still other embodiments, each $R_a$ and $R_b$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy. In some embodiments, each aryl or heteroaryl of $R_1$ is optionally substituted with one or more groups independently selected from halo, hydroxy, nitro, cyano, trifluoromethyl, trifluoromethoxy, mercapto, carboxy, $(C_1\text{-}C_{20})$alkyl, $(C_2\text{-}C_{20})$alkenyl, $(C_2\text{-}C_{20})$alkynyl, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, aryl$(C_1\text{-}C_{20})$alkyl, heteroaryl$(C_1\text{-}C_{20})$alkyl, aryl$(C_2\text{-}C_{20})$alkenyl, aryl$(C_2\text{-}C_{20})$alkynyl, heteroaryl$(C_2\text{-}C_{20})$alkenyl, heteroaryl$(C_2\text{-}C_{20})$alkynyl, $(C_1\text{-}C_{20})$alkanoyloxy, $(C_2\text{-}C_{20})$alkenoyloxy, and $(C_2\text{-}C_{20})$alkynoyloxy.

In certain embodiments, $R_1$ is a $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl is substituted with hydroxy, mercapto, carboxy or $NR_aR_b$. In other embodiments, $R_1$ is a $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl is substituted with hydroxy. In yet other embodiments, $R_1$ is a $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl is substituted on the carbon adjacent to the triple bond in Formula (I) with hydroxy. In still other embodiments, $R_1$ is a $(C_5\text{-}$ $C_{10}$)alkyl, ($C_2$-$C_{10}$)alkenyl, or ($C_2$-$C_{10}$)alkynyl that is substituted with hydroxy, mercapto, carboxy, or $NR_aR_b$. In some embodiments, $R_1$ is a ($C_5$-$C_{10}$)alkyl, ($C_2$-$C_{10}$)alkenyl, or ($C_2$-$C_{10}$)alkynyl that is substituted with hydroxyl. In certain embodiments, $R_1$ is a ($C_5$-$C_{10}$)alkyl, ($C_2$-$C_{10}$)alkenyl, or ($C_2$-$C_{10}$)alkynyl that is substituted on the carbon adjacent to the triple bond in Formula (I) with hydroxy. In some embodiments, $R_1$ is a ($C_5$-$C_{10}$)alkyl that is substituted with hydroxy, mercapto, carboxy or $NR_aR_b$. In other embodiments, $R_1$ is a ($C_5$-$C_{10}$)alkyl that is substituted with hydroxy. In still other embodiments, $R_1$ is a ($C_5$-$C_{10}$)alkyl that is substituted on the carbon adjacent to the triple bond in Formula (I) with hydroxy. In yet other embodiments, $R_1$ is ($C_1$-$C_{20}$)alkyl, ($C_2$-$C_{20}$)alkenyl, or ($C_2$-$C_{20}$)alkynyl, which ($C_1$-$C_{20}$)alkyl, ($C_2$-$C_{20}$)alkenyl, or ($C_2$-$C_{20}$)alkynyl is substituted with ($C_1$-$C_{20}$)alkanoyloxy. In some embodiments, $R_1$ is a ($C_5$-$C_{10}$)alkyl that is substituted on the carbon adjacent to the triple bond in Formula (I) with ($C_1$-$C_{20}$) alkanoyloxy. In yet other embodiments, $R_1$ is 1-hydroxyhexane, 1-hydroxy-2,2-dimethylpropane, 1-acetoxyhexane or cis-1-hydroxy-3-hexane. In certain embodiments, $R_1$ is a ($C_5$-$C_{10}$)alkyl that is substituted on the carbon adjacent to the triple bond in Formula (I) with acetoxy.

In other embodiments, $R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, or $CCl_3$. In certain embodiments, each $R_c$ and $R_d$ is independently H, ($C_1$-$C_{20}$)alkyl, ($C_1$-$C_{20}$)alkanoyl, ($C_2$-$C_{20}$)alkenylcarbonyl, ($C_2$-$C_{20}$)alkynylcarbonyl, ($C_1$-$C_{20}$)alkoxy, ($C_2$-$C_{20}$)alkenyloxy, or ($C_2$-$C_{20}$)alkynyloxy. In yet other embodiments, $R_e$ is ($C_1$-$C_{20}$)alkyl, ($C_1$-$C_{20}$)alkanoyl, ($C_2$-$C_{20}$)alkenylcarbonyl, ($C_2$-$C_{20}$)alkynylcarbonyl, ($C_1$-$C_{20}$)alkoxy, ($C_2$-$C_{20}$)alkenyloxy, or ($C_2$-$C_{20}$)alkynyloxy. In other embodiments, $R_2$ is $CF_2Br$, $CFHBr$, $CF_2Cl$, or $CFHCl$. In yet other embodiments, $R_2$ is $CF_2Br$.

In certain embodiments, the compound of Formula (I) is a compound of Formula (II):

(II)

In some embodiments, $R_3$ is hydroxy, mercapto, chloro, bromo, methylthio, ethylthio, methoxy, ethoxy, acetylamino, ($C_1$-$C_{10}$)alkanoyloxy, arylcarbonyloxy, or aryloxy. In certain embodiment, $R_4$ is ($C_4$-$C_{10}$)alkyl, ($C_2$-$C_{10}$)alkenyl, or ($C_2$-$C_{10}$)alkynyl, which ($C_4$-$C_{10}$)alkyl, ($C_2$-$C_{10}$)alkenyl, or ($C_2$-$C_{10}$)alkynyl is optionally substituted with one or more groups independently selected from halo, hydroxy, mercapto, ($C_1$-$C_{10}$)alkoxy, ($C_1$-$C_{10}$)alkylthio, carboxy, ($C_1$-$C_{10}$) alkoxycarbonyl, aryl, heteroaryl, and $NR_aR_b$. In still other embodiments, each $R_a$ and $R_b$ is independently H, ($C_1$-$C_{20}$) alkyl, ($C_1$-$C_{20}$)alkanoyl, ($C_2$-$C_{20}$) alkenylcarbonyl, ($C_2$-$C_{20}$) alkynylcarbonyl, ($C_1$-$C_{20}$)alkoxy, ($C_2$-$C_{20}$)alkenyloxy, ($C_2$-$C_{20}$) alkynyloxy, or aryl-($C_1$-$C_{20}$)alkoxycarbonyl. In yet other embodiments, each $R_a$ and $R_b$ is independently H, ($C_1$-$C_{20}$)alkyl, ($C_1$-$C_{20}$)alkanoyl, ($C_2$-$C_{20}$)alkenylcarbonyl, ($C_2$-$C_{20}$)alkynylcarbonyl, ($C_1$-$C_{20}$)alkoxy, ($C_2$-$C_{20}$)alkenyloxy, or ($C_2$-$C_{20}$)alkynyloxy.

In other embodiments, $R_3$ is hydroxy, mercapto, chloro, bromo, methylthio, ethylthio, methoxy, ethoxy, or acetylamino.

In some embodiments, $R_4$ is ($C_4$-$C_{10}$)alkyl, ($C_2$-$C_{10}$) alkenyl, or ($C_2$-$C_{10}$)alkynyl, which ($C_4$-$C_{10}$)alkyl, ($C_2$-$C_{10}$) alkenyl, or ($C_2$-$C_{10}$)alkynyl is optionally substituted with one or more groups independently selected from halo, hydroxy, mercapto, ($C_1$-$C_{10}$)alkoxy, ($C_1$-$C_{10}$)alkylthio, carboxy, ($C_1$-$C_{10}$)alkoxycarbonyl, aryl, heteroaryl, and $NR_aR_b$. In other embodiments, $R_4$ is ($C_4$-$C_{10}$)alkyl that is optionally substituted with one or more groups independently selected from halo, hydroxy, mercapto, ($C_1$-$C_{10}$)alkoxy, ($C_1$-$C_{10}$) alkylthio, carboxy, ($C_1$-$C_{10}$)alkoxycarbonyl, aryl, heteroaryl, and $NR_aR_b$. In still other embodiments, $R_4$ is ($C_4$-$C_{10}$)alkyl that is optionally substituted with one or more groups independently selected from halo, hydroxy, mercapto, carboxy, ($C_1$-$C_{10}$)alkoxycarbonyl, and $NR_aR_b$. In yet other embodiments, $R_4$ is ($C_4$-$C_{10}$)alkyl. In certain embodiments, $R_4$ is ($C_4$-$C_6$)alkyl.

In some embodiments, the compounds of Formula (I) can be selected from those specified in Table 1.

TABLE 1

| Compound Number (alternative designation) | Compound Structure |
|---|---|
| I-1 (XB-05, or XB05, or BX11) | 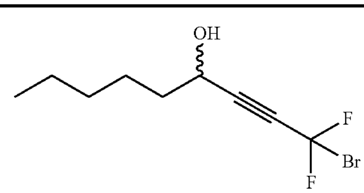 |
| I-2 (JAB-4-169 or XB-05a or BX12 or LD-01-072 or TM0112) | 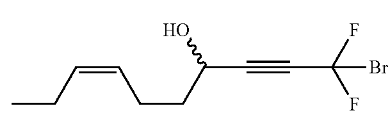 |

TABLE 1-continued
| Compound Number (alternative designation) | Compound Structure |
|---|---|
| I-3 (XB-05b or BX17 or TMO-117 or MNR-3-43) | 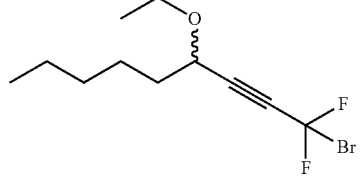 |
| I-4 (MNR-3-86) | 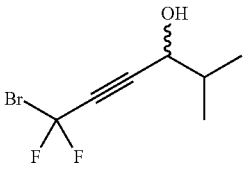 |
| I-5 (MNR-3-85) | 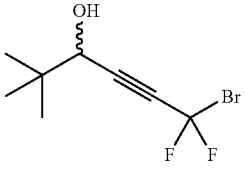 |
| I-6 | 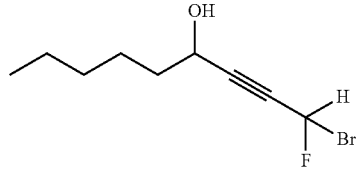 |
| I-7 | 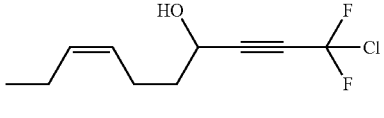 |
| I-8 | 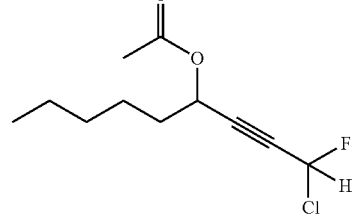 |
| I-9 | 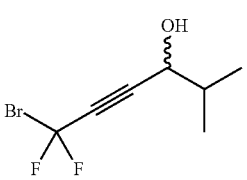 |
| I-10 | 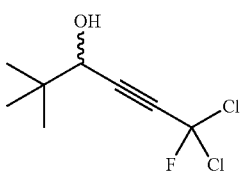 |

TABLE 1-continued

| Compound Number (alternative designation) | Compound Structure |
| --- | --- |
| I-11 (1-Octyn-3-ol) | 1-octyn-3-ol: HO–CH(C₅H₁₁)–C≡C–H |
| I-12 (JAB-4-155) | MeO–CH(C₅H₁₁)–C≡C–CF$_2$Br |
| I-13 (JAB-4-156) | HO–CH(C₅H₁₁)–C≡C–CF$_3$ |
| I-14 (JAB-4-158) | H–CH(C₅H₁₁)–C≡C–CF$_2$Br (1-bromo-1,1-difluoro-2-nonyne) |
| I-15 (JAB-4-163) | C₅H₁₁–C(=O)–C≡C–CF$_2$Br |
| I-16 (JAB-4-165) | C₅H₁₁–C(=O)–CH=C(NHPr)–CF$_2$Br |
| I-17 (MNR-1-102) | Cl–CH(C₅H₁₁)–C≡C–CF$_2$Br |
| I-18 (MNR-1-110) | HO–CH(C₅H₁₁)–C≡C–CF$_2$–O–C$_6$H$_4$–F (para) |

TABLE 1-continued
| Compound Number (alternative designation) | Compound Structure |
|---|---|
| I-19 (MNR-1-111) | 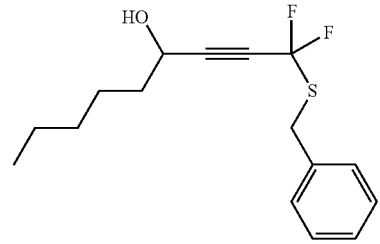 [SMILES: CCCCCC(O)C#CC(F)(F)SCc1ccccc1] |
| I-20 (MNR-1-117) | 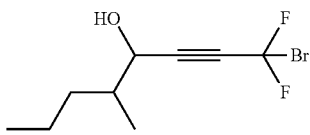 |
| I-21 (MNR-1-118) | 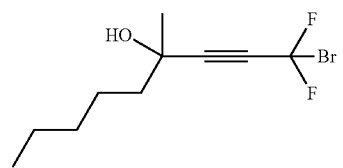 |
| I-22 (MNR-1-122) | 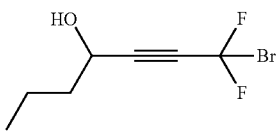 |
| I-23 (MNR-1-129) | 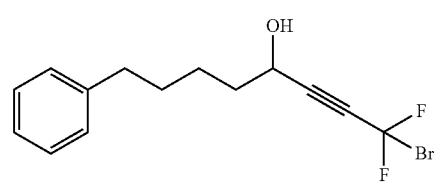 [SMILES: OC(C#CC(F)(F)Br)CCCCc1ccccc1] |
| I-24 (MNR-1-147) | 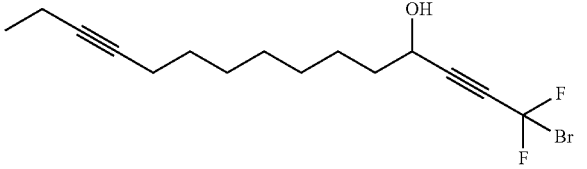 [SMILES: CCC#CCCCCCCCC(O)C#CC(F)(F)Br] |
| I-25 (MNR-1-186) | 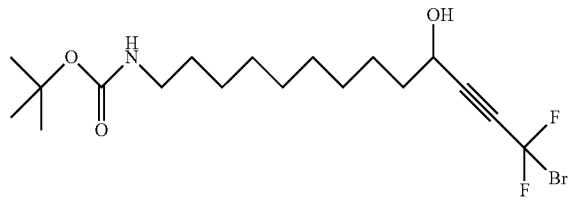 [SMILES: CC(C)(C)OC(=O)NCCCCCCCCCC(O)C#CC(F)(F)Br] |
| I-26 (MNR-1-191) | 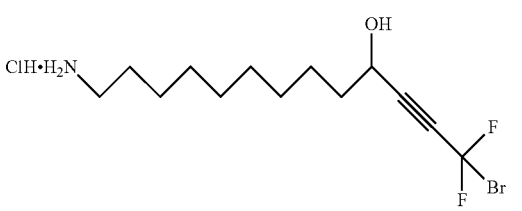 |

TABLE 1-continued

| Compound Number (alternative designation) | Compound Structure |
| --- | --- |
| I-27 (MNR-2-6) | Biotin-C(=O)-NH-CH₂CH₂-O-CH₂CH₂-O-CH₂CH₂-O-CH₂CH₂-O-CH₂CH₂-C(=O)-NH-(CH₂)₉-CH(OH)-C≡C-CF₂Br |
| I-28 (MNR-3-38) | (R)-HO-CH(hexyl)-C≡C-CF₂Br |
| I-29 (MNR-3-41) | (S)-HO-CH(hexyl)-C≡C-CF₂Br |
| I-30 (MNR-3-91) | HO-CH(hexyl)-C≡C-CHF₂ |
| I-31 (MNR-3-93) | HO-CH(phenyl)-C≡C-CF₂Br |
| I-32 (MNR-3-90) | HO-CH(cyclohexyl)-C≡C-CF₂Br |
| I-33 (MNR-3-82) | HO-CH(CH₂CH₂-phenyl)-C≡C-CF₂Br |
| I-34 (MNR-3-92) | HO-CH(hexyl)-C≡C-CH₂Br |

TABLE 1-continued

| Compound Number (alternative designation) | Compound Structure |
|---|---|
| I-35 (MNR-3-27) | (structure: tetrahydropyranyl ether of a secondary alcohol bearing an alkyl chain and a –C≡C–CF₂Br group) |
| I-36 (MNR-3-94) | (structure: HO–CH(alkyl chain)–C≡C–CF₂Br) |
| I-37 (MNR-3-69) | (structure: HO–CH(longer alkyl chain)–C≡C–CF₂Br) |
| I-38 (MNR-3-89) | (structure: HO–CH(longest alkyl chain)–C≡C–CF₂Br) |

In some embodiments, the invention includes one or more of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, or I-38. In some embodiments, the invention includes one or more of I-1, I-2, I-3, I-20, I-22, I-24, I-28, I-32, I-33, I-35, I-36, I-37, or I-38. In some embodiments, the invention includes one or more of I-1, I-2, I-3, I-22, or I-28. In some embodiments, the invention includes one or more of I-1, I-2, I-3, or I-28. In some embodiments, the invention includes one or more of I-1, I-2, or I-3. In some embodiments, the invention includes one or more of I-1 or I-2.

In some embodiments, one or more of compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, or I-38 are excluded from the invention. In other embodiments, one or more of compounds I-4, I-5, I-6, I-7, I-8, I-9, I-10, I-11, I-12, I-13, I-14, I-15, I-16, I-17, I-18, I-19, I-21, I-23, I-25, I-26, I-27, I-29, I-30, I-31, or I-34 are excluded from the invention. In other embodiments, one or more of compounds I-6, I-7, I-8, I-9, or I-10 are excluded from the invention. In other embodiments, compound I-4 is excluded from the invention.

In some embodiments, the compounds of Formula (I) (e.g., Formula (II), I-1, I-2, I-3, I-22, or I-28) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, derivatives of the compounds (e.g., ethers, esters, or amides) which have desirable retention and release characteristics, but which are hydrolyzed (e.g., easily hydrolyzed) by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In other embodiments, compounds encompass Formula (I) and salts, optical isomers, geometric isomers, salts of isomers, and derivatives thereof.

In certain embodiments, one or more compounds (e.g., Formula (I), Formula (II), I-1, I-2, I-3, I-22, or I-28) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds (e.g., Formula (I), Formula (II), I-1, I-2, I-3, I-22, or I-28) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds (e.g., Formula (I), Formula (II), I-1, I-2, I-3, I-22, or I-28). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

In some embodiments, one or more compounds (e.g., Formula (I), Formula (II), I-1, I-2, I-3, I-22, or I-28) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., Formula (I), Formula (II), I-1, I-2, I-3, I-22, or I-28) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one compound (e.g., Formula (I), Formula (II), I-1, I-2, I-3, I-22, or I-28) that is effective to treat the disease, condition, or disorder that the organism has, or is suspected of having, or is susceptible to, or to bring about a desired physiological effect. In some embodiments, the composition or pharmaceutical composition comprises at least one compound (e.g., Formula (I), Formula (II), I-1, I-2, I-3, I-22, or I-28) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, it is possible to employ many concentrations in the methods of the present invention, and using, in part, the guidance provided herein, one could adjust and test any number of concentrations in order to find one that achieves the desired result in a given circumstance. In other embodiments, the compounds (e.g., Formula (I), Formula (II), I-1, I-2, I-3, I-22, or I-28) can be administered in combination with one or more other therapeutic agents for a given disease, condition, or disorder.

In some embodiments, the compositions can include a unit dose of one or more compounds (e.g., Formula (I), Formula (II), I-1, I-2, I-3, I-22, or I-28) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Administration Routes and Treatments of Disease

The compounds (e.g., Formula (I), Formula (II), I-1, I-2, I-3, I-22, or I-28) can be administered to animals by any number of suitable administration routes or formulations. The compounds (e.g., Formula (I), Formula (II), I-1, I-2, I-3, I-22, or I-28) can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds (e.g., Formula (I), Formula (II), I-1, I-2, I-3, I-22, or I-28) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., cancer), and the severity of the disease (e.g., stage or severity of cancer). Of course, combinations of administration routes can be administered, as desired.

Some embodiments of the invention include a method for providing a subject with a composition comprising one or more compounds (e.g., Formula (I), Formula (II), I-1, I-2, I-3, I-22, or I-28) described herein (e.g., a pharmaceutical composition) which comprises one or more administrations of one or more such compositions; the compositions may be the same or different if there is more than one administration.

Some embodiments of the invention include a method for treating an animal for cancer, comprising: (a) determining a level of MGST1 (microsomal glutathione S-transferase 1) in a sample comprising cancer cells from an animal having a cancer; and (b) administering one or more compositions (e.g., a pharmaceutical composition) comprising a compound, wherein the compositions may be the same or different if there is more than one administration. Determining the level of MGST1 can be accomplished using any suitable measurement of the level of MGST1 including but not limited to any measurement disclosed herein, measuring the extent of expression of MGST1 in a cell (or cell population), measuring the extent of activity of MGST1 in a cell (or cell population), or measuring the amount of MGST1 in a cell (or cell population). Determining the level of MGST1 can be accomplished by any suitable method such as but not limited to a method comprising western blot analysis or immunoblot analysis. The sample comprising cancer cells from the animal (e.g., human, rat, mouse, rabbit, or monkey) can be obtained using any suitable technique such as but not limited to biopsy (e.g., core needle, punch, or surgical biopsy) or collecting cells from bodily fluids (e.g., blood, lymph, urine, or mucus). The administering step can be accomplished using any suitable method, such as but not limited to those disclosed herein.

Some embodiments of the invention include a method for treating an animal for cancer, comprising: (a) determining a level of MGST1 (microsomal glutathione S-transferase 1) in a sample comprising cancer cells from an animal having a cancer; and (b) if the level of MGST1 in the sample is different (e.g., higher or lower) than the level of MGST1 in a control sample then the animal is administered one or more compositions (e.g., a pharmaceutical composition) comprising a compound, wherein the compositions may be the same or different if there is more than one administration. In other embodiments, the administering step is only performed if the MGST1 level in the sample is higher compared to the level of MGST1 in the control sample. In other embodiments, the control sample can be any suitable sample such as but not limited to non-cancer cells from an animal (e.g., the same animal or the same species of animal), cancer cells from an animal (e.g., the same animal or the same species of animal), cancer cells from an animal that are not chemoresistant cancer cells (e.g., the same animal or the same species of animal), or cancer cells from an animal that are not cancer-therapy-resistant cancer cells (e.g., the same animal or the same species of animal). In some embodiments, the level of MGST1 in the control sample can be a single determination, multiple determinations (e.g., a triplet), or an average of many determinations (e.g., using one animal or many animals over a single period of time or over multiple periods of time). In other embodiments, the level of MGST1 in the control sample can be determined at the same or similar time (e.g., seconds, minutes, hours, etc.) as the level of MGST1 in the sample. In still other embodiments, the level of MGST1 in the control sample can be determined at a different time (e.g., days, weeks, months, years etc.) as the level of MGST1 in the sample. In certain embodiments, the level of MGST1 in the control sample provides a reference level of MGST1. In other embodiments, the administering step is only performed if the MGST1 level in the sample is higher compared to a reference level of MGST1.

Microsomal glutathione S-transferase 1 is a membrane-localized enzyme (e.g., mitochondrial and ER). In certain embodiments, MGST1 is involved in detoxifying xenobiotics. In other embodiments, MGST1 is involved in mitigating oxidative stress (e.g., caused by lipid peroxidation products). In some embodiments, MGST1 is overexpressed in cancers cells (e.g., in chemo-resistant cancer cells and/or in cancer-therapy-resistant cancer cells). In still other embodiments, MGST1 is overexpressed in liver cells. Information on human protein and gene sequences for MGST1 can be found at UniProtKB-P10620 (MGST1_HUMAN), which is herein incorporated by reference in its entirety. Information on mouse protein and gene sequences for MGST1 can be found at UniProtKB-Q91VS7 (MGST1_MOUSE), which is herein incorporated by reference in its entirety.

Diseases that can be treated in an animal (e.g., mammals, porcine, canine, avian (e.g., chicken), bovine, feline, primates, rodents, monkeys, rabbits, mice, rats, and humans) using a compound (e.g., Formula (I), Formula (II), I-1, I-2, I-3, I-22, or I-28) include, but are not limited to cancers.

In some embodiments, cancers that can be treated in an animal (e.g., mammals, porcine, canine, avian (e.g., chicken), bovine, feline, primates, rodents, monkeys, rabbits, mice, rats, and humans) using a compound (e.g., Formula (I), Formula (II), I-1, I-2, I-3, I-22, or I-28) include, but are not limited to, acute lymphoblastic leukemia, astrocytoma, basal cell carcinoma, bladder cancer, bone marrow cancer, brain cancer, breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated include, but are not limited to, basal cell carcinoma, bladder cancer, bone marrow cancer, brain cancer, breast cancer, CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated include, but are not limited to, leukemia, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof. In some embodiments, cancers that can be treated include, but are not limited to, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof. In some embodiments, cancers that can be treated include, but are not limited to, cancerous tumors. In some embodiments, cancers that can be treated include, but are not limited to, chemo-resistant cancers or cancer-therapy-resistant cancers. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In certain embodiments, cancers that can be treated include, but are not limited to, chemo-resistant cancers or cancer-therapy-resistant cancers. In some instances, cancer-therapy-resistant cancers can be any cancer that is or has become (e.g., after a cancer treatment) resistant (e.g., less effective) to a cancer therapy, such as one or more cancer therapies becoming less effective over time after the start of the one or more cancer therapies. In other embodiments, the cancer-therapy-resistant cancers is a chemo-resistant cancer. A chemo-resistant therapy can, for example, be any chemo-therapy that is or has become resistant (e.g., less effective) to a chemotherapy, such as one or more chemotherapies becoming less effective over time after the start of the one or more chemotherapies. Chemo-resistant cancers or cancer-therapy-resistant cancers can be a result of any mechanism including but not limited to mutations (e.g., that alter the functions of genes), point mutations, changes in the epigenetics, changes in the epigenetic signals, changes in expression of genes, or changes in metabolism (e.g., in response to chemotherapy).

In some embodiments, cancers that can be treated in an animal (e.g., mammals, porcine, canine, avian (e.g., chicken), bovine, feline, primates, rodents, monkeys, rabbits, mice, rats, and humans) using a compound (e.g., Formula (I), Formula (II), I-1, I-2, I-3, I-22, or I-28) include, but are not limited to cancers that do not use an increase in reactive oxidative species as a mechanism to kill or cancer cells that have an increase in MGST1 level (e.g., activity, expression, or amount).

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof), treating can include but is not limited to prophylactic treatment and therapeutic treatment. As such, treatment can include, but is not limited to: preventing cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); reducing the risk of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); ameliorating or relieving symptoms of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); eliciting a bodily response against cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); inhibiting the development or progression of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); inhibiting or preventing the onset of symptoms associated with cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); reducing the severity of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); causing a regression of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof) or one or more of the symptoms associated with cancer (e.g., a decrease in tumor size); causing remission of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof); or preventing relapse of cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof). In some embodiments, treating does not include prophylactic treatment of cancer (e.g., preventing or ameliorating future cancer).

Treatment of an animal can occur using any suitable administration method (such as those disclosed herein) and using any suitable amount of a compound (e.g., Formula (I), Formula (II), I-1, I-2, I-3, I-22, or I-28). In some embodiments, methods of treatment comprise treating an animal for cancer (e.g., chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof). Some embodiments of the invention include a method for treating a subject (e.g., an animal such as a human or primate) with a composition comprising a compound (e.g., Formula (I), Formula (II), I-1, I-2, I-3, I-22, or I-28) (e.g., a pharmaceutical composition) which comprises one or more administrations of one or more such compositions; the compositions may be the same or different if there is more than one administration.

In some embodiments, the method of treatment includes administering an effective amount of a composition comprising a compound (e.g., Formula (I), Formula (II), I-1, I-2, I-3, I-22, or I-28). As used herein, the term "effective amount" refers to a dosage or a series of dosages sufficient to affect treatment (e.g., to treat cancer, such as but not limited to chemo-resistant cancer, cancer-therapy-resistant cancer, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, brain cancer, breast cancer, or cancerous tumors thereof) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound (e.g., Formula (I), Formula (II), I-1, I-2, I-3, I-22, or I-28) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound (e.g., Formula (I), Formula (II), I-1, I-2, I-3, I-22, or I-28) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound (e.g., Formula (I), Formula (II), I-1, I-2, I-3, I-22, or I-28) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound (e.g., Formula (I), Formula (II), I-1, I-2, I-3, I-22, or I-28) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing tumor size). A therapeutically effective amount can be administered in one or more administrations. For some purposes of this invention, a therapeutically effective amount is an amount appropriate to treat an indication (e.g., to treat cancer). By treating an indication is meant achieving any desirable effect, such as one or more of palliate, ameliorate, stabilize, reverse, slow, or delay disease (e.g., cancer) progression, increase the quality of life, or to prolong life. Such achievement can be measured by any suitable method, such as but not limited to measurement of tumor size.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound (e.g., Formula (I), Formula (II), I-1, I-2, I-3, I-22, or I-28) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound (e.g., Formula (I), Formula (II), I-1, I-2, I-3, I-22, or I-28) can be used as adjuvant with other chemotherapeutic agents. The use of a compound (e.g., Formula (I), Formula (II), I-1, I-2, I-3, I-22, or I-28) can, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections associated with cancer). In other embodiments, intravenous immunoglobulin (IVIG) therapy can be used as part of the treatment regime (i.e., in addition to administration of the compound(s) of the invention).

The presently-disclosed subject matter is further illustrated by the following specific but non-limiting examples. The following examples may include compilations of data that are representative of data gathered at various times during the course of development and experimentation related to the present invention.

EXAMPLES

Some data related to the inventions are described below. Information (e.g., regarding compounds and methods) can be found in WO 2008/098077 A2 (which is herein incorporated by reference in its entirety), US 2008/0188570 A1 (which is herein incorporated by reference in its entirety), U.S. Pat. No. 9,383,364 B2 (which is herein incorporated by reference in its entirety), and U.S. Pat. No. 9,737,493 B2 (which is herein incorporated by reference in its entirety).

Example Set A

Materials and Methods

Materials. XB05 was prepared as previously described (X U et al. "An efficient synthesis of difluoropropargyl bromides Synthesis" (2006) Vol. 5, pp. 803-806, which is herein incorporated by reference in its entirety). XB05 and other compounds were prepared in the Medicinal Chemistry facility of the James Graham Brown Cancer Center (Louisville, Ky.). MGST1 antibody (ab131059) was purchased from Abcam (Cambridge, UK), while GAPDH (sc-365062) and secondary antibodies (sc-2030, sc-2005) were purchased from Santa Cruz Biotechnology (Dallas, Tex.). 3-(4,5-dimethylthiazol-2-yl)-2,5-diphenyltetrazolium bromide (MTT), DTNB, cysteine, reduced glutathione, diethylmaleate, and maleimide were all purchased from Sigma. LentiCRISPR v2 was a gift from Feng Zhang (Addgene plasmid #52961).

Cell culture. A549 and IMR-90 cells were purchased from the American Type Culture Collection (ATCC), while HOP-62 and HOP-92 were obtained from the cell line repository at the National Cancer Institute. Cells were grown in the appropriate medium supplemented with 10% fetal bovine serum (FBS, Life Technologies, Grand Island, N.Y.), 62.5 µg/mL penicillin and 100 µg/mL streptomycin (Life Technologies) in a humidified incubator at 37° C. with 5% CO2. The media were as follows: Dulbecco's modified Eagle's medium (DMEM, Life Technologies) for A549 cells; RPMI 1640 (Life Technologies) for HOP-62 and HOP-92 cells; Eagle's minimal essential medium (EMEM) with Eagle's balanced salt solution (EBSS), 2 mM L-glutamine, 1500 mg/L sodium bicarbonate (Lonza, Walkersville, Md.), supplemented with 1 mM sodium pyruvate (Life Technologies) and non-essential amino acids (Life Technologies) for IMR-90 cells. Cell lines were verified with a 9-marker short tandem repeat profile and inter-species contamination test (Idexx BioResearch), although A549 cells utilized in proliferation assays were missing the Y allele at the amelogenin marker.

Making an A549 cell line that constitutively expresses CAS9. LentiCAS9-blast vector was transfected into HEK293T cells along with pVSVG and psPAX2 as directed by Addgene. Briefly 6 µg of lentiCAS9-blast was cotransfected with 3 µg of psPAX2 and 1.5 µg pVSVG with 3/1 ratio of Polyethylenimine (PEI) into HEK293T cells in a 10 cm plate with cells at 30% confluence. Media containing lentivirus was collected 36 hr after transfection and continued every 12 hr for 48 hrs. Media containing virus was used to infect A549 cells in the presence of 4 µg/ml of polybrene with cells at 25% confluence. Cells were grown for 48 hr after infection and then treated with blasticidin (50 µg/ml) for 48 hr before cells were plated at low density for isolation of single clones. Single clones were isolated and level of CAS9 expression was measured by western blot. The clone with the highest levels of CAS9 expression was used for subsequent experiments for infection of virus containing of gRNA against the whole genome.

Preparing gRNA virus for infection of CAS9-expressing A549 cells. Human genomic scale CRISPR Knockout (GeCKO) v2.0 pooled libraries A and B in lentiGuide-Puro were cotransfected in HEK293T cells along with pVSVG and psPAX2 as directed by Addgene. Briefly 236 µg of both library A and B separately were cotransfected with 157 µg of psPAX2 and 79 µg VSVG with 3/1 ratio of PEI into (10) 15 cm plate each for A and B libraries of HEK293T with cells at 30% confluence. Media containing lentivirus was collected 36 hr after transfection and continued every 12 hr for 48 hrs. Virus titer was determined as described by Addgene. Titer of LentiGuide-Puro virus was 1.91E6 and 2.4E6 infectable units of virus for A and B viruses for A549 cells, respectively.

Infection of CAS9 expressing A549 cells with A and B library virus and treating with XB05. The human GeCKO V2.0 library targets 19,050 genes with 3 gRNAs per gene in both library A and B for a total of 6 gRNAs per gene. There are 1864 miRNAs targeted with 4 gRNAs per miRNA, and an additional 1000 control (non-targeting) gRNAs in the combined library. This provides a total of 123,411 total gRNAs in the combined library. Approximately 300 cells were infected with each gRNA for a total of over 37 million cells being infected. We infected at a multiplicity of infection of 0.3 to minimize the likelihood of one cell getting more than one gRNA. Thus, 124 million cells were utilized per experiment with enough A/B virus to infect 30% of the cells (37 million infectable units) with 4 µg/ml of polybrene. Forty-eight hours after infection, cells were treated with 1.5 µg/ml puromycin for an additional 48 hrs. After puromycin selection, cells were trypsinized and counted. One sixth of the cells (65 million) in duplicate were centrifuged, and pellets were stored at −80° C. for the initial time point. The remaining cells were split into 4 groups for duplicate treatment with 1 µM XB05 (IC30 value of XB05 in A549 cells) or vehicle (DMSO) for roughly 20 cells doublings. Cells were passaged with or without XB05 roughly every 4 days during the treatment.

DNA isolation, PCRs and sequencing of Genomic DNA from Cells. Genomic DNA was isolated from the initial time point (2 days post puromycin treatment), and from XB05 or vehicle treated cells after 20 cell doublings using Blood & Cell Culture DNA Maxi Kit (Qiagen, Hilden, Germany). DNA was quantitated, and 64 PCR reactions (100 µl each), containing 4 µg genomic DNA each were performed for each data point to enable representation of the library. Hercules II Fusion DNA Polymerase (Agilent, Santa Clara, Calif.) was used, and PCR reactions were performed as directed by the manufacturer. Primers are shown in Table A1. Ten different forward primers that were mixed in equal ratios to create diversity were used for subsequent sequencing.

TABLE A1

Primers for Initial PCR Reactions

| | |
|---|---|
| MiSEQ F1 | TCGTCGGCAGCGTCAGATGTGTATAAGAGACAGNNNNNNNN NNNNNNNTCTTGTGGAAAGGACGAAACACCGVAC (SEQ ID NO: 1) |
| MiSEQ F2 | TCGTCGGCAGCGTCAGATGTGTATAAGAGACAGNNNNNNNN NNNNNNTCTTGTGGAAAGGACGAAACACC GVAC (SEQ ID NO: 2) |
| MiSEQ F3 | TCGTCGGCAGCGTCAGATGTGTATAAGAGACAGNNNNNNNN NNNNNTCTTGTGGAAAGGACGAAACACC GVAC (SEQ ID NO: 3) |
| MiSEQ F4 | TCGTCGGCAGCGTCAGATGTGTATAAGAGACAGNNNNNNNN NNNNTCTTGTGGAAAGGACGAAACACC GVAC (SEQ ID NO: 4) |
| MiSEQ F5 | TCGTCGGCAGCGTCAGATGTGTATAAGAGACAGNNNNNNNN NNNTCTTGTGGAAAGGACGAAACACC GVAC (SEQ ID NO: 5) |
| MiSEQ F6 | TCGTCGGCAGCGTCAGATGTGTATAAGAGACAGNNNNNNNN NNTCTTGTGGAAAGGACGAAACACC GVAC (SEQ ID NO: 6) |
| MiSEQ F7 | TCGTCGGCAGCGTCAGATGTGTATAAGAGACAGNNNNNNNN NTCTTGTGGAAAGGACGAAACACC GVAC (SEQ ID NO: 7) |
| MiSEQ F8 | TCGTCGGCAGCGTCAGATGTGTATAAGAGACAGNNNNNNNN TCTTGTGGAAAGGACGAAACACC GVAC (SEQ ID NO: 8) |
| MiSEQ F9 | TCGTCGGCAGCGTCAGATGTGTATAAGAGACAGNNNNNNNT CTTGTGGAAAGGACGAAACACC GVAC (SEQ ID NO: 9) |
| MiSEQ F10 | TCGTCGGCAGCGTCAGATGTGTATAAGAGACAGNNNNNNTC TTGTGGAAAGGACGAAACACC GVAC (SEQ ID NO: 10) |
| MiSEQ REV | gtctcgtgggctcggagatgtgtataagagacagTATGTCT ACTATTCTTTCCCCTGCACTGTA (SEQ ID NO: 11) |

"N" can be A, G, C or T

The PCR conditions were 95° for 2 min followed by 25 cycles of 95° C. for 10 sec, 55° C. for 20 sec and 72° C. for 30 sec followed by 72° C. for 3 min.

Following the initial PCR the 64 replicates for each data point were combined, and 25 µl of the PCR product mixture was purified using AMPure XP beads (Beckman Coulter, Brea, Calif.) and used as a template for second indexing PCR using the Nextera XT DNA Library Preparation Kit (San Diego, Calif.) according to manufacturer's protocol. The second indexing PCR product was purified with AMPure XP beads (Beckman Coulter) prior to denaturing, dilution and sequencing using the NextSeq 500/550 75 cycle High Output Kit v2 (Illumina, San Diego, Calif.) on the NextSeq 500 System (Illumina).

Western blotting. Equal amounts of protein per sample were resolved using 4-20% Tris-glycine gels (Life Technologies) and then transferred onto PVDF membranes (Thermo Fisher, Waltham, Mass.) in Tris-glycine buffer containing 20% methanol. Membranes were blocked with 5% milk in TBS containing 0.01% Tween 20 (Thermo Fisher). Protein levels were detected using the following dilutions of antibodies: MGST1, 1:1000; GAPDH, 1:2000; secondary antibodies, 1:10,000. When necessary, membranes were stripped with Restore Plus western blot stripping buffer (Thermo Fisher) prior to being reprobed.

Cell proliferation & viability assays. Anti-proliferative activity of XB05 and other compounds was evaluated using a previously published 3-(4,5-dimethylthiazol-2-yl)-2,5-diphenyltetrazolium bromide (MTT) assay protocol (MORGAN "Tetrazolium (MTT) assay for cellular viability and activity" Methods Mol Biol. (1998) Vol. 79, pp. 179-83, which is herein incorporated by reference in its entirety, BATES et al. "Antiproliferative activity of G-rich oligonucleotides correlates with protein binding" J Biol Chem. (1999) Vol. 274, No. 37, pp. 26369-26377, which is herein incorporated by reference in its entirety, SALIPUR et al. "A novel small molecule that induces oxidative stress and selectively kills malignant cells" Free Radic Biol Med. (2014) Vol. 68, pp. 110-121, which is herein incorporated by reference in its entirety). Cells were seeded in quadruplicate wells in 96-well plates and allowed to adhere overnight. To account for intrinsic differences in growth rates, cells were plated at the following densities to achieve comparable MTT absorbance values (OD570 between 0.5 and 1) for untreated cells: A549 and HOP-62, 1000 cells/well; HOP-92, 2500 cells/well; IMR-90, 5000 cells/well. After 72 hrs of treatment with XB05 or other compounds, MTT (Sigma, St. Louis, Mo.) was added for 4 hrs prior to cell lysis. Each assay was performed in at least triplicate.

Cell viability was determined by trypan blue exclusion. A549 cells were seeded at a density of 3000 cells/well in 24-well plates and allowed to adhere overnight. After 72 hrs of treatment with XB05 or other compounds, cells were visualized by microscopy, while cell count and viability was determined in triplicate for each sample using 0.4% trypan blue solution (Life Technologies) and the TC10 Automated Cell Counter (BioRad, Hercules, Calif.).

Dithiobis-2-nitrobenzioc acid (DTNB) assay for free sulfhydryls. Similar to previously described in SALIPUR et al. "A novel small molecule that induces oxidative stress and selectively kills malignant cells" Free Radic Biol Med. (2014) Vol. 68, pp. 110-121, which is herein incorporated by reference in its entirety, reactivity with free sulfhydryls was evaluated using DTNB (Sigma). Briefly, a 4× solution of DTNB (6 mM DTNB, 50 mM sodium acetate in 100 mM Tris-HCl, pH 8.0) and solutions of 0.5 mM cysteine (Sigma) and reduced glutathione (GSH, Sigma) in 100 mM Tris-HCl, pH 8.0 were freshly prepared. The 200 mM stock solutions of XB05, other compounds, diethylmaleate (Sigma), and maleimide (Sigma) were prepared in 100% DMSO, and subsequently diluted to 2× working solutions in 100 mM Tris-HCl, pH 8.0. Thiol compounds (final concentration 0.25 mM) and thiol-reactive compounds (final concentrations 0.04-5 mM) or vehicle were added in duplicate to a 96-well plate and incubated for 30 min at 37° C. DTNB solution was then added to each well (final concentration 400 µM), and incubated at room temperature for an additional 5 min. Absorbance at 412 nm was determined by a Biotek HT Synergy plate reader (Winooski, Vt.).

Statistical analysis. Graphs were prepared, and ANOVA and t-tests were performed with GraphPad Prism® 6 software (GraphPad Software, Inc., La Jolla, Calif.).

Results

NCI60 human tumor cell line screen of XB05 activity. To further investigate the initial observations of XB05's anticancer activities, XB05 was submitted to the National Cancer Institute's Developmental Therapeutics Program for testing with the NCI60 human tumor cell line panel. This panel consists of 60 well-characterized human tumor cell lines (SHOEMAKER "The NCI60 human tumour cell line anticancer drug screen" Nat Rev Cancer (2006) Vol. 6, No. 10, Vol. 813-823, which is herein incorporated by reference in its entirety). The NCI60 data (See FIG. 1) indicated that XB05 had activity against about one-third of cancer cells, whereas other cell lines in the screen has less activity (up to 1000-fold less sensitive). The results also revealed that XB05 has an unusual pattern of activity in the NCI60 screen—unlike any other existing cancer drug—indicating a novel mechanism of action.

The COMPARE algorithm was used to probe microarray results from the cell lines to identify gene expression that correlated with this unusual pattern of growth inhibition. Microsomal glutathione-S transferase 1 (MGST1) appeared as the top correlation with total growth inhibition (TGI) data. MGST1 is a 17.3 kDa glutathione transferase (GST) that is present in mitochondria and ER. MGST1 expression can sometimes be associated with drug resistance than drug sensitivity. MGST1 can sometimes protect cells from lipid peroxidation and/or oxidative stress.

Figure 2:
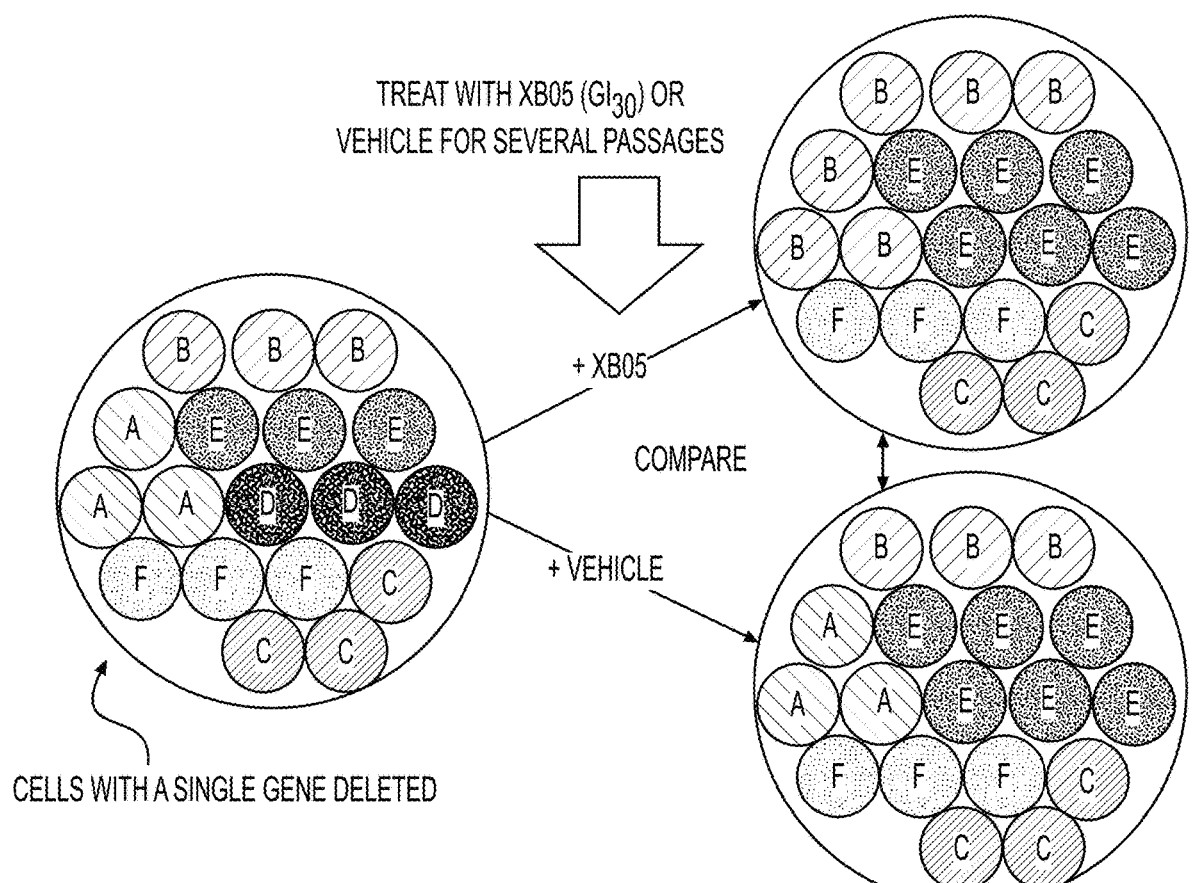
FIG. 2: Screens to Identify the role of MGST1. Illustration of the genome-wide CRISPR-Cas 9 screen. A pool of cells is created that have single genes (A, B, C, etc.) deleted by CRISPR/Cas9. These are grown in the presence of XB05 to generate XB05 resistant cells. Sequencing identifies gene deletions that make cells more resistant to XB05 (e.g. gene B, overrepresented in resistant cells) or more sensitive (e.g. gene A, underrepresented in resistant cells). The results of the CRISPR-Cas9 whole genome screen for genes that influence response to XB05 indicate a role for MGST1.

FIG. 2 illustrates the genome-wide CRISPR-Cas9 screen for genes that modify response to XB05. The top correlate in the genome-wide screen of genes that sensitize cancer cells to XB05 was also MGST1 (data not shown). Multiple gRNAs for this gene were enriched in the XB05-resistant cells by an average of about 10-fold, indicating that MGST1 provides a higher XB05 activity.

Figure 3:
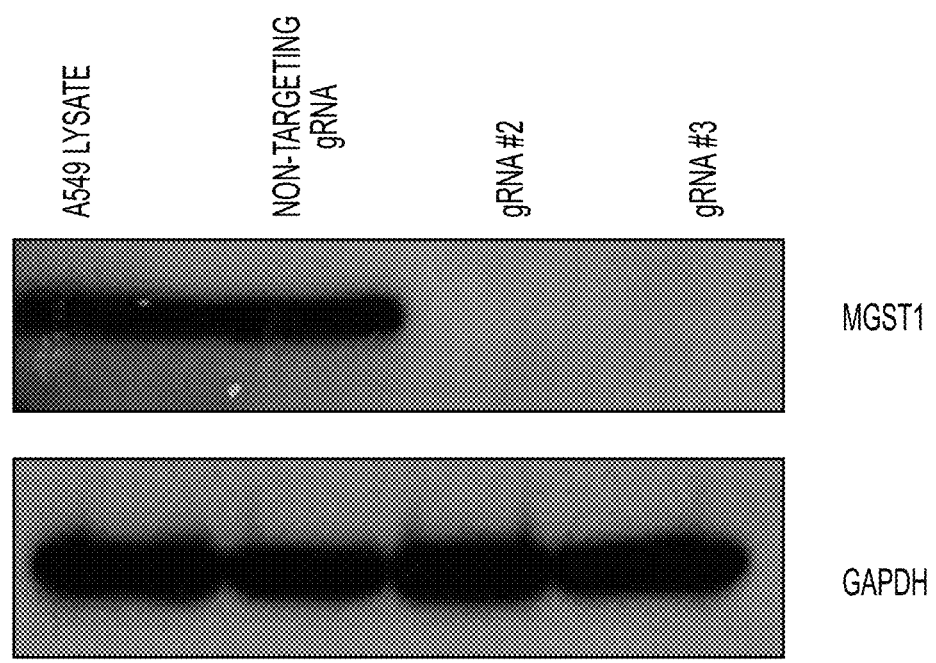
FIG. 3: To assess the role of MGST1 in XB05 activity, we engineered MGST1 knockout cells using CRISPR/Cas9 technology. Western blot analysis indicating the knockout of MGST1 in A549 cells.
Figure 4:
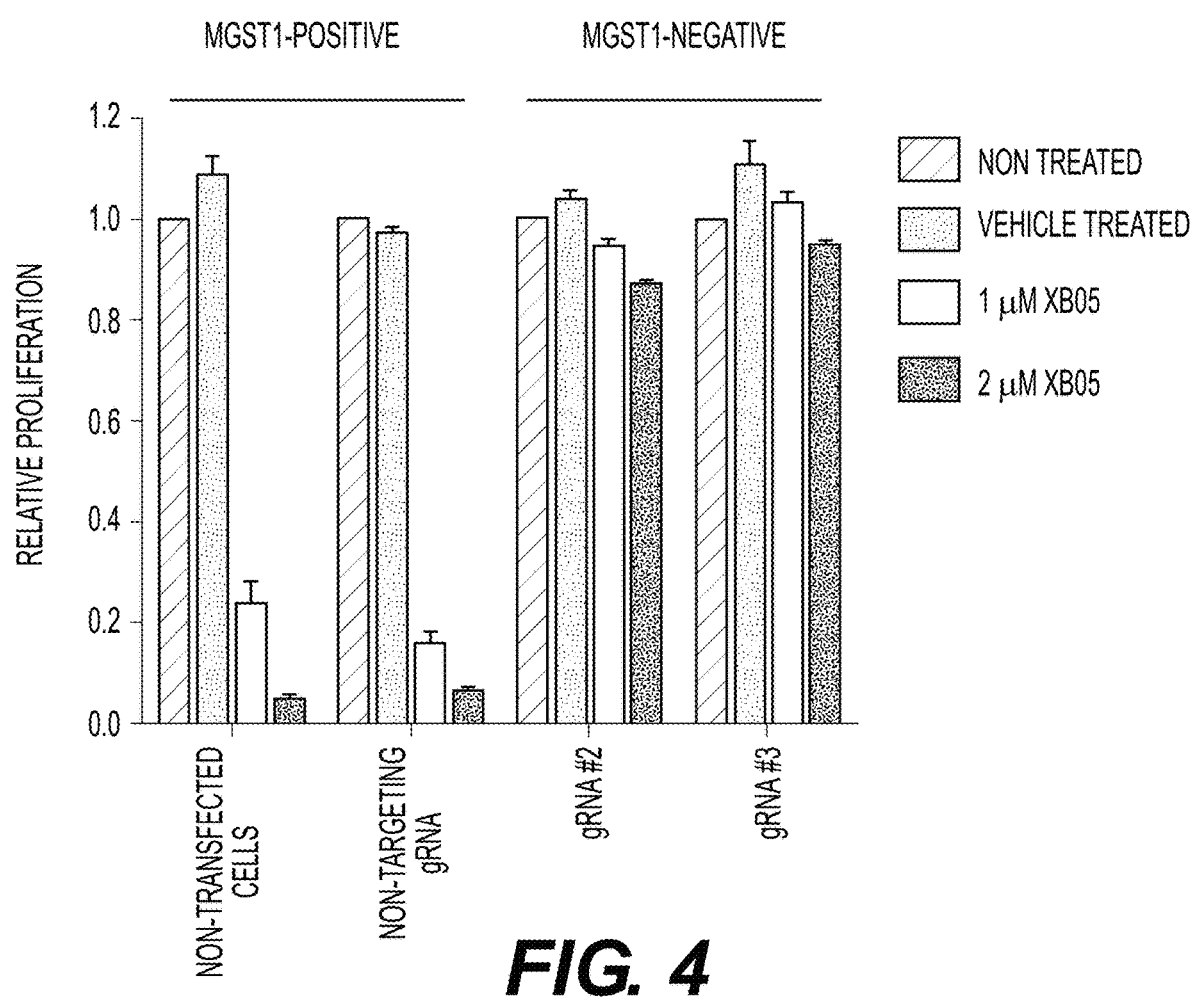
FIG. 4: To assess the role of MGST1 in XB05 activity, we engineered MGST1 knockout cells using CRISPR/Cas9 technology. Effect of XB05 treatment (72 h) on the relative proliferation of two independent clones of A549 cancer cells that express MGST1 (non-transfected, non-targeting gRNA) or where MGST1 was knocked out (gRNA #2, gRNA 3).

In order to validate the results of the whole genome screen, MGST1 knockout cell lines were created using CRISPR-Cas9 technology and treated with XB05 (FIG. 3 and FIG. 4). In non-transfected A549 cells and A549 cells transfected with non-targeting gRNA, treatment with 1 and 2 μM XB05 caused cell proliferation to decrease to approximately 20% and 5% of vehicle, respectively. After knockout of MGST1 using two different gRNAs sequences, the effect of XB05 on cell proliferation was reversed indicating that MGST1 provides a higher XB05 activity (FIG. 3 and FIG. 4).

Structure-activity relationship. In order to better characterize XB05 and to provide insight into the mechanism of action, a structure-activity relationship study was conducted. XB05 and other compounds were synthesized by a modified literature procedure (X U et al. "An efficient synthesis of difluoropropargyl bromides" Synthesis (2006) Vol. 5 (2006), pp. 803-806, which is herein incorporated by reference in its entirety, SALIPUR et al. "A novel small molecule that induces oxidative stress and selectively kills malignant cells" Free Radic Biol Med. (2014) Vol. 68, pp. 110-21, which is herein incorporated by reference in its entirety). MNR-3-28 and MNR-3-41 were prepared from commercially available, enantiomerically pure propargyl alcohols and enantiomeric excess was determined via Mosher ester analysis (HOYE et al. "Mosher ester analysis for the determination of absolute configuration of stereogenic (chiral) carbinol carbons" Nat Protoc. (2007) Vol. 2, No. 10, pp. 2451-2458, which is herein incorporated by reference in its entirety). JAB-4-155 and MNR-3-43 were prepared by treating XB05 with either methyl iodide or acetyl chloride in the presence of base. JAB-4-163 was prepared by oxidation of XB05 with Dess-Martin periodinane. MNR-3-91 was synthesized by treating XB05 with n-butyllithium and quenching with aqueous ammonium chloride. Likewise, MNR-1-102 was prepared by treating XB05 with N-chlorosuccinimide and triphenylphosphine. JAB-4-156 (YAMAZAKI et al., "Modified Preparation Method of Trifluoromethylated Propargylic Alcohols and Its Application to Chiral 2, 6-Dideoxy-6, 6, 6-trifluoro sugars" J. Org. Chem. (1995) Vol. 60, No. 19, pp. 6046-6056, which is herein incorporated by reference in its entirety), MNR-3-92 (YOSHIDA et al. "Palladium-catalysed cascade ring expansion reaction of cyclobutanols that have a propargylic moiety with nucleophiles" Org Biomol Chem. (2004) Vol. 2, No. 21, pp. 3099-3107, which is herein incorporated by reference in its entirety), MNR-1-110 (LIU et al., "Efficient synthesis of unsymmetrical S-(bromodifluoromethyl)diarylsulfonium salts for electrophilic bromodifluoromethylating reagents" New J. Chem. (2012) Vol. 36, pp. 1769-1773, which is herein incorporated by reference in its entirety) and MNR-1-111 (LIU et al., "Efficient synthesis of unsymmetrical S-(bromodifluoromethyl)diarylsulfonium salts for electrophilic bromodifluoromethylating reagents" New J. Chem. (2012) Vol. 36, pp. 1769-1773, which is herein incorporated by reference in its entirety) were synthesized from modified literature procedures, as indicated.

XB05 and related compounds were assessed for antiproliferative activity in malignant (A549) and non-malignant (IMR-90) cells (Table A2).

TABLE A2

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| XB05 | (structure: HO-CH(C5H11)-C≡C-CF2Br with F,F,Br) | 0.4 | 2.5 | ND | ND |
| 1-Octyn-3-ol | (structure: HO-CH(C5H11)-C≡C-H) | ND | ND | ND | Reactive |
| JAB-4-155 | (structure: MeO-CH(C5H11)-C≡C-CF2Br) | 3.5 | ND | ND | ND |
| JAB-4-156 | (structure: HO-CH(C5H11)-C≡C-CF3) | ND | ND | ND | ND |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| JAB-4-158 | [structure: CF₂Br alkyne with hexyl chain and H] | 2.1 | ND | ND | ND |
| JAB-4-163 | [structure: CF₂Br alkyne ketone with hexyl chain] | ND | ND | ND | ND |
| JAB-4-165 | [structure: CF₂Br alkene with HN-propyl, ketone, hexyl chain] | ND | ND | ND | ND |
| JAB-4-169/ XB05a/ TM0112 | [structure: CF₂Br alkyne with OH and allyl/pentenyl chain] | 0.4 | 3.8 | ND | ND |
| MNR-1-102 | [structure: CF₃ alkyne with CBr, Cl and pentyl chain] | ND | ND | Reactive | ND |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-1-110 | 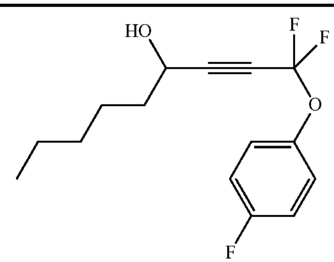 | ND | ND | ND | ND |
| MNR-1-111 | 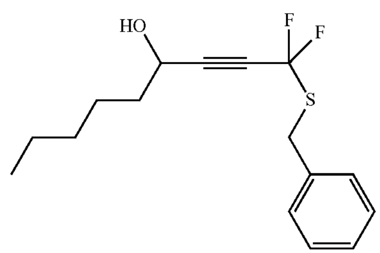 [SMILES: CCCCCC(O)C#CC(F)(F)SCc1ccccc1] | ND | ND | ND | ND |
| MNR-1-117 | 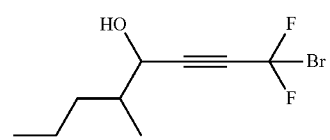 | 1.9 | 7.9 | ND | ND |
| MNR-1-118 | 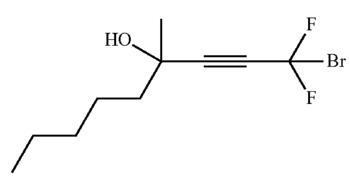 | 8.2 | ND | ND | ND |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-1-122 | | 0.8 | 1.1 | ND | ND |
| MNR-1-129 | | ND | ND | | |
| MNR-1-147 | | 1.1 | 4.0 | | |
| MNR-1-186 | | ND | ND | | |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-1-191 | *structure* | ND | ND | | |
| MNR-2-6 | *structure* | ND | ND | | |
| MNR-3-38 | *structure* | 0.4 | 1.5 | ND | ND |
| MNR-3-41 | *structure* | 4.8 | ND | ND | ND |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-3-91 | 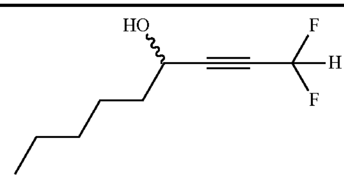 | ND | ND | | |
| MNR-3-43 | 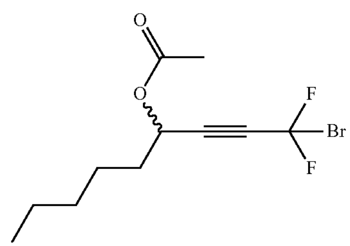 [SMILES: CCCCCC(C#CC(F)(F)Br)OC(C)=O] | 0.9 | 5.4 | ND | ND |
| MNR-3-86 | 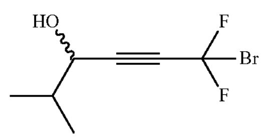 | ND | ND | | |
| MNR-3-85 | 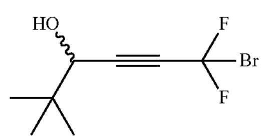 | ND | ND | | |
| MNR-3-93 | 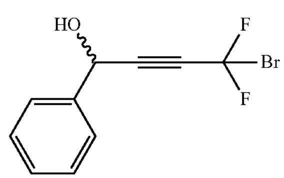 [SMILES: OC(C#CC(F)(F)Br)c1ccccc1] | ND | ND | | |

TABLE A2-continued

Summary of XB05-related Compound Activity and Thiol Reactivity

| Cpd ID | Structure | MTT Antiproliferative Activity - IC50 (μM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-3-90 | | 0.9 | 3.1 | | |
| MNR-3-82 | | 1.2 | 2.8 | | |
| MNR-3-92 | | 7.1 | 8.7 | Reactive | Reactive |
| MNR-3-27 | | 1.9 | 3.7 | | |

TABLE A2-continued

Summary of XB05-related Compound Activity and Thiol Reactivity

| Cpd ID | Structure | MTT Antiproliferative Activity - IC50 (µM) | | DTNB Reactivity with Thiols | |
|---|---|---|---|---|---|
| | | A549 (lung adenocarcinoma) | IMR0 (non-malignant lung fibroblasts) | DTNB assay with Glutathione | DTNB assay with Cysteine |
| MNR-3-94 | [structure] | 0.9 | 2.7 | | |
| MNR-3-69 | [structure] | 1.0 | 2.8 | | |
| MNR-3-89 | [structure] | 1.1 | 2.7 | | |

Figure 5:
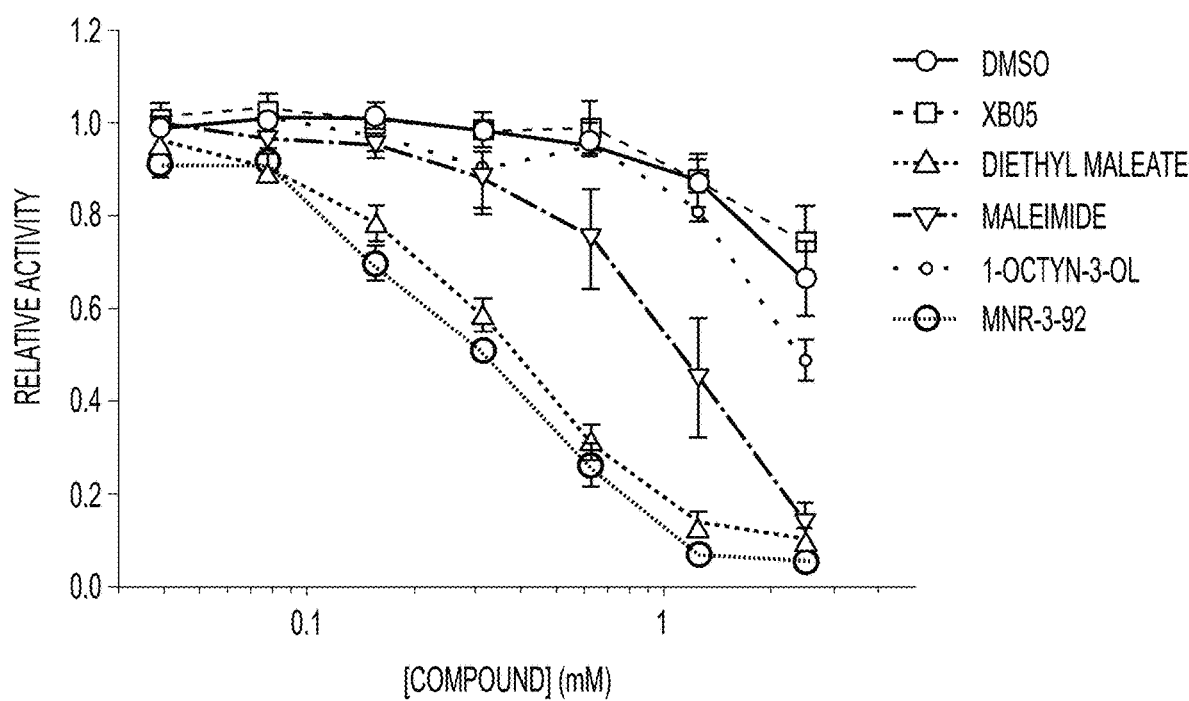
FIG. 5: DTNB assays to evaluate XB05 and other compound reactivity with free thiols—Reaction with cysteine.
Figure 6:
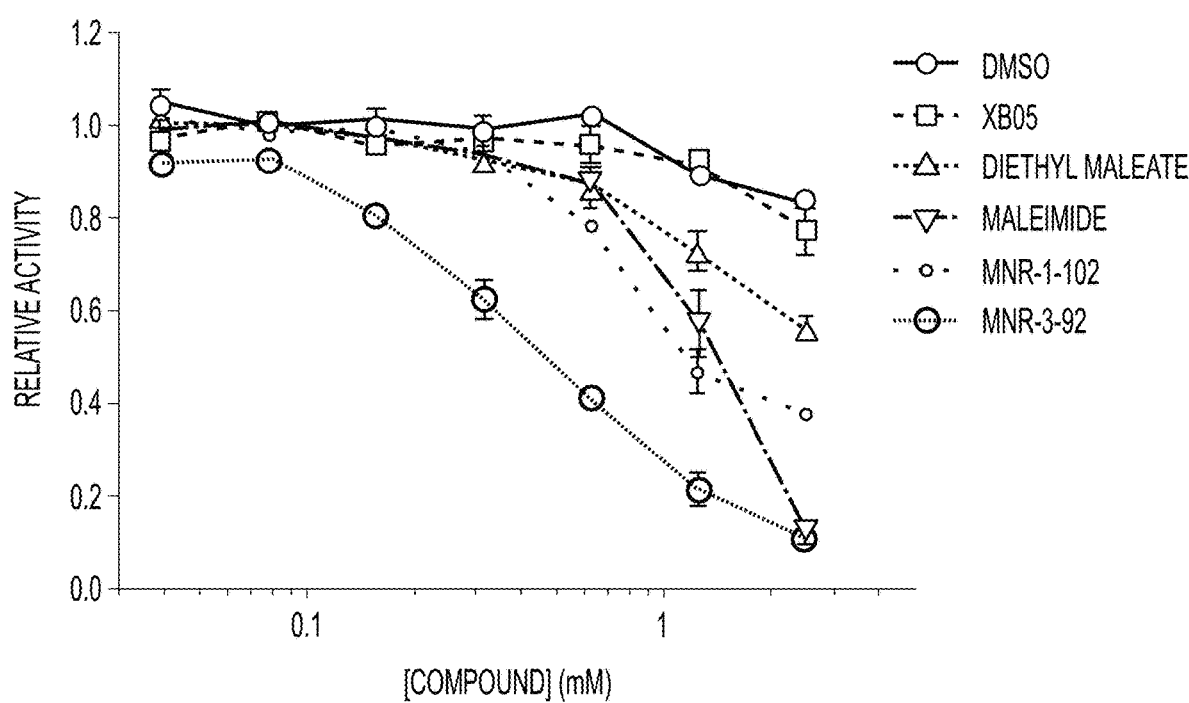
FIG. 6: DTNB assays to evaluate XB05 and other compound reactivity with free thiols—Reaction with reduced glutathione.

MTT ND - not detected at concentrations up to 10 µM
DTNB ND - not detected at concentrations up to 2.5 mM Compounds were evaluated for reactivity with the thiols present on cysteine and glutathione (Table A2). XB05 was not reactive with either thiol-containing compound (FIG. 5 and FIG. 6). While a few compounds (e.g., 1-octyn-3-ol, replacement of the hydroxyl with Cl, and replacement of the F with H) had some reactivity with either cysteine or glutathione, thiol reactivity of most compounds did not appear to be related to the anti-proliferative effects observed in cells.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A method for treating an animal for cancer, comprising determining a level of MGST1 (microsomal glutathione S-transferase) in a sample comprising cancer cells from the animal having a cancer; and administering to the animal one or more compositions comprising a compound, if the level of MGST1 in the sample is higher than the level of MGST1 in a control sample, wherein (a) determining a level of MGST1 comprises one or more of measuring the extent of expression of MGST1 in the sample, measuring the extent of activity of MGST1 in the sample, or measuring the amount of MGST1 in the sample (b) the compositions may be the same or different if there is more than one administration, (c) the control sample comprises non-cancer cells, and (d) the compound is

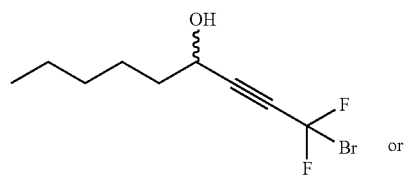
(XBO5)

or

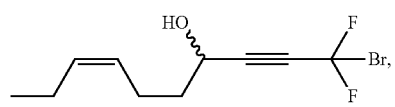
(XBO5a)

or a salt thereof.

2. The method of claim 1, wherein the compound is

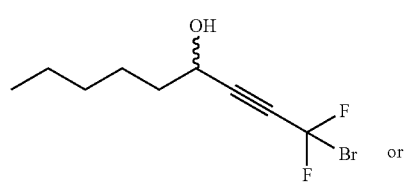
(XBO5)

or (XBO5a)

3. The method of claim 1, wherein the compound is

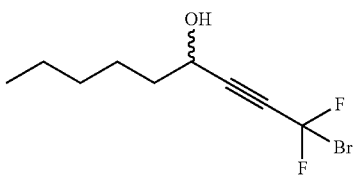
(XBO5)

or a salt thereof.

4. The method of claim 1, wherein the compound is

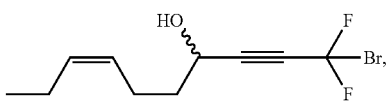
(XBO5a)

or a salt thereof.

5. The method of claim 1, wherein the compound is

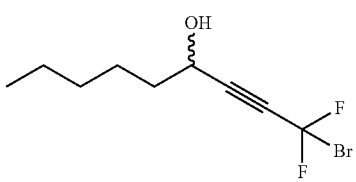
(XBO5)

6. The method of claim 1, wherein the compound is (XBO5a)

7. The method of claim 1, wherein at least one of the one or more compositions further comprises a formulary ingredient.

8. The method of claim 1, wherein at least one of the one or more compositions comprises is a pharmaceutical composition.

9. The method of claim 1, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

10. The method of claim 1, wherein if there is more than one administration at least one composition used for at least one administration is different from the composition of at least one other administration.

11. The method of claim 1, wherein the compound of at least one of the one or more compositions is administered to the animal in an amount of from about 0.005 mg/kg animal body weight to about 50 mg/kg animal body weight.

12. The method of claim 1, wherein the animal is a human, a rodent, or a primate.

13. The method of claim 1, wherein the animal is in need of the treatment.

14. The method of claim 1, wherein the method is for treating colon cancer, NSCLC, CNS cancer, pancreatic cancer, breast cancer, renal cancer, ovarian cancer, melanoma, leukemia, lymphoma, or cancerous tumors thereof.

15. The method of claim 1, wherein the method is for treating colon cancer, NSCLC, CNS cancer, pancreatic cancer, breast cancer, renal cancer, ovarian cancer, melanoma, leukemia, or lymphoma.

16. The method of claim 1, wherein the method is for treating colon cancer, NSCLC, CNS cancer, breast cancer, renal cancer, ovarian cancer, melanoma, or cancerous tumors thereof.

17. The method of claim 1, wherein the method is for treating colon cancer, NSCLC, CNS cancer, breast cancer, renal cancer, or cancerous tumors thereof.

18. The method of claim 1, wherein the method is for treating leukemia, NSCLC, colon cancer, ovarian cancer, melanoma, or cancerous tumors thereof.

19. The method of claim 1, wherein the method is for treating colon cancer, NSCLC, or cancerous tumors thereof.

20. The method of claim 1, wherein the method is for treating colon cancer.

21. The method of claim 1, wherein the method is for treating NSCLC.

* * * * *